United States Patent
Labbe et al.

(10) Patent No.: US 9,282,747 B2
(45) Date of Patent: Mar. 15, 2016

(54) ANTIMICROBIAL AND ANTI-INFLAMMATORY ACTIVITY OF SWITCHGRASS-DERIVED EXTRACTIVES

(71) Applicant: UNIVERSITY OF TENNESSEE RESEARCH FOUNDATION, Knoxville, TN (US)

(72) Inventors: Nicole Labbe, Knoxville, TN (US); Bonnie H. Ownley, Knoxville, TN (US); Kimberly D. Gwinn, Knoxville, TN (US); Naima Moustaid-Moussa, Lubbock, TX (US); Doris H. D'Souza, Knoxville, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 14/079,015

(22) Filed: Nov. 13, 2013

(65) Prior Publication Data

US 2014/0134668 A1   May 15, 2014

Related U.S. Application Data

(60) Provisional application No. 61/726,000, filed on Nov. 13, 2012.

(51) Int. Cl.
| | |
|---|---|
| *A01N 65/00* | (2009.01) |
| *C10G 3/00* | (2006.01) |
| *A61K 36/899* | (2006.01) |
| *A23L 1/30* | (2006.01) |
| *A01N 65/40* | (2009.01) |
| *C10L 1/02* | (2006.01) |

(52) U.S. Cl.
CPC ................ *A01N 65/00* (2013.01); *A01N 65/40* (2013.01); *A23L 1/3002* (2013.01); *A61K 36/899* (2013.01); *C10G 3/00* (2013.01); *C10L 1/02* (2013.01); *A23V 2002/00* (2013.01); *A61K 2236/33* (2013.01); *C10G 2300/1014* (2013.01); *C12P 2201/00* (2013.01)

(58) Field of Classification Search
None
See application file for complete search history.

(56) References Cited

FOREIGN PATENT DOCUMENTS

JP        09268106 A    * 10/1997

OTHER PUBLICATIONS

Vu, Andrea L. Identifying pathogens of switchgrass and investigating antimicrobial activity of switchgrass-derived extractives. Masters Thesis. [online]. [retrieved on Feb. 23, 2015]. Retrieved from the Internet: < URL: http://trace.tennessee.edu/cgi/viewcontent.cgi?article=2230&context=utk_gradthes>).*
English Derwent Abstract for JP 09268106 A. Oct. 14, 1997.*
Uppalapati, SR et al. Pathogenicity of Pseudomonas syringae pv. tomato on tomato seedlings: Phenotypic and gene expression analyses of the virulence function of coronatine. Molecular Plant-Microbe Interactions. 2008. 21(4): 383-395.*
Hu, Z et al. Biomass characterization of morphological portions of Alamo switchgrass. Journal of Agricultural and Food Chemistry. 2011. 59: 7765-7772.*
Chawla, A. S. et al. "Anti-Inflammatory Action of Ferulic Acid and Its Esters in Carrageenan Induced Rat Paw Oedema Model," *Indian Journal of Experimental Biology*, Mar. 1987, pp. 187-189, vol. 25.
Chen, S.-F. et al. "Compositional Analysis of Water-Soluble Materials in Corn Stover," *J. Agric. Food Chem.*, 2007, pp. 5912-5918, vol. 55.
Chen, S.-F. et al. "Compositional Analysis of Water-Soluble Materials in Switchgrass," *J. Agric. Food Chem.*, 2010, pp. 3251-3258, vol. 58.
Tao, L. et al. "Process and technoeconomic analysis of leading pretreatment technologies for lignocellulosic ethanol production using switchgrass," *Bioresource Technology*, 2011, pp. 11105-11114, vol. 102.
Thammasouk, K. et al. "Influence of Extractives on the Analysis of Herbaceous Biomass," *J. Agric. Food Chem.*, 1997, pp. 437-443, vol. 45.
Uppugundla, N. et al. "Switchgrass Water Extracts: Extraction, Separation and Biological Activity of Rutin and Quercitrin," *J. Agric. Food Chem.*, 2009, pp. 7763-7770, vol. 57.
Yan, J. et al. "Chemical compositions of four switchgrass populations," *Biomass and Bioenergy*, 2010, pp. 48-53, vol. 34.

* cited by examiner

*Primary Examiner* — Renee Claytor
*Assistant Examiner* — Susan E Fernandez
(74) *Attorney, Agent, or Firm* — Saliwanchik, Lloyd & Eisenschenk

(57) ABSTRACT

Switchgrass is an increasingly important biofuel crop, but knowledge of switchgrass fungal pathogens is not extensive. The purpose of this research was to identify the fungal pathogens that decrease crop yield of switchgrass grown in Tennessee and to investigate a potential sustainable disease management strategy from a value-added by-product of the switchgrass biofuel conversion process. The specific objectives were 1) to identify and characterize prevalent fungal pathogens of switchgrass in Tennessee, 2) assess switchgrass seed produced in the United States for seedborne fungal pathogens, and 3) evaluate switchgrass extractives for antimicrobial activity against plant pathogens.

3 Claims, 9 Drawing Sheets
(7 of 9 Drawing Sheet(s) Filed in Color)

ANTIMICROBIAL AND ANTI-INFLAMMATORY ACTIVITY OF SWITCHGRASS-DERIVED EXTRACTIVES

CROSS-REFERENCE TO RELATED APPLICATION

This application claims the benefit of U.S. Provisional Application Ser. No. 61/726,000, filed Nov. 13, 2012, the disclosure of which is hereby incorporated by reference in its entirety, including all figures, tables and amino acid or nucleic acid sequences.

This invention was made with United States government support under Department of Energy contract DE-EE0002993. The United States government has certain rights in the invention.

BACKGROUND OF THE INVENTION

Switchgrass (*Panicum virgatum* L.) is a perennial native grass currently being investigated for use in production of cellulosic ethanol. Biofuel (cellulosic ethanol) from switchgrass has a low production cost and results in 540% more renewable energy than nonrenewable energy consumed (Schmer et al. 2008). Additionally, estimated greenhouse gas emissions from switchgrass-based cellulosic ethanol are 94% lower than estimated greenhouse gas emissions from gasoline (Schmer et al. 2008). The ethanol is produced through a biochemical process that uses various enzymes to convert the switchgrass cellulose to ethanol. To maximize the efficiency of this process, the plant extractives can be removed to allow for optimum enzyme activity (N. Labbé, personal communication, Anderson and Akin 2007). Switchgrass extractives are high in phenolic compounds (such as p-coumaric, ferulic, and sinapic acids), which are associated with the induction of the systemic resistance response that plants exhibit in the presence of pathogens or other stresses (Chen et al. 2010).

Although switchgrass-derived cellulosic ethanol production is a main focus of the biofuels initiative in Tennessee, limited research has been done on plant pathogens that occur on switchgrass grown in the state. As expansive monocultures of switchgrass are developed for commercial production, disease pressure is likely to increase due to lack of plant biodiversity (Wolfe 2000, Etheridge et al. 2001).

Host: *Panicum virgatum*

Switchgrass (*Panicum virgatum* L.) is a perennial, warm-season ($C_4$) tall prairie grass that has been adopted as a crop in the last 50 years (Parrish and Fike 2005). Switchgrass can grow up to 3 meters in height in one growing season and possesses a diffuse panicle seedhead with two-flowered spikelets at the end of long branches (Bouton 2008). Most switchgrass genotypes are caespitose (grow in small, dense clumps) and develop short rhizomes that allow the plant to form a loose sod over time (Bouton 2008). Switchgrass is native to North America and is adapted to a wide geographical range, spanning from 20° to 60° north latitude and east of 100° west longitude to the Atlantic seaboard (Vogel 2004). Two predominant ecotypes have developed: lowlands and uplands (Brunken and Estes 1975, Porter 1966, Vogel 2004). Basic chromosome number for both ecotypes is 9, but the somatic chromosome number is usually tetraploid in lowland selections and octaploid in uplands (Bouton 2008). Soil acidity typically is not a factor in switchgrass growth, but increased water-holding capacity as related to soil texture is necessary for stand establishment (Parrish and Fike 2005).

Several studies have demonstrated the importance of vesicular-arbuscular mycorrhizae in nutrient uptake for switchgrass (Clark and Zeto 2000, Hetrick et al. 1988, Boerner 1992, Brejda et al. 1998, Wilson et al. 2001). Brejda et al. (1998) tested growth and nutrient uptake in response to natural versus sterilized rhizosphere soil conditions. Switchgrass grown in soil with rhizosphere fungi and bacteria produced 15-fold greater overall biomass, showed 6-fold greater nitrogen recovery and 36-fold greater phosphorus recovery than plants grown in sterile soil (Brejda et al. 1998). In several reviews, it has been suggested that mycorrhizae may mediate plant responses to drought stress, nutrient deficiencies, toxic metals, and pathogen attack (Parrish and Fike 2005).

Pathogens

More than 75 fungal pathogens occur on switchgrass in the United States (Farr and Rossman 2011). Close to 150 fungal isolates have been identified on switchgrass, but pathogenicity of many of these has not been determined (Ghmire et al. 2011, Gravert and Munkvold 2002). Twenty-four species of plant-parasitic nematodes, including species of *Dorylaimida*, *Triplonchida*, and *Tylenchida* and five viruses (Panicum mosaic virus, Barley yellow dwarf virus, Sugarcane mosaic virus, Wheat soil-borne mosaic virus, and Maize rayado fino virus) have been reported on switchgrass in the United States (Agindotan et al. 2010, Cassida et al. 2005, Farr and Rossman 2011, Garrett et al. 2004, Mekete et al. 2011, Sill 1957). In Tennessee, prior to published results of the current study, only one fungal disease had been reported: rust caused by *Puccinia emaculata* (Zale et al. 2008). The lack of reports of pathogens in Tennessee does not indicate a lack of presence. In 2008, researchers at the University of Tennessee found *Tilletia pulcherrima* (the causal agent of bunt disease) on switchgrass seed that had been produced in Texas and distributed to growers in Tennessee (Carris et al. 2008). Based on reports from other regions in the United States (Farr and Rossman 2011), genera of fungal pathogens that are likely to occur in Tennessee include *Alternaria, Bipolaris, Curvularia*, and *Fusarium*.

*Alternaria* species can be difficult to identify due to conidial plasticity and low genetic variability among species (Misaghi et al. 1978, Kusaba and Tsunge 1995, Pryor and Gilbertson 2000). *Alternaria* includes nearly 100 species of dematiaceous mitosporic fungi that occur worldwide and range from general saprophytes to specific plant pathogens of cereals, ornamentals, nuts, vegetables, and fruits, including citrus (Thomma 2003). Spore production can be induced in the laboratory by use of specific culture media and environmental conditions (Shahin and Shephard 1979). Differential media assays have been developed for some *Alternaria* spp. (Andersen et al. 2001). Molecular identity can be confirmed by analysis of the internal transcribed spacer (ITS) region and mitochondrial small subunit (SSU) ribosomal DNA (Kusaba and Tsunge 1995, Pryor and Gilbertson 2000), or by random amplified polymorphic DNA (RAPD) analysis (Pryor and Gilbertson 2002, Roberts et al. 2000). Some anamorphic *Alternaria* species are associated with the teleomorphic genus *Lewia*, which is a member of the family Pleosporaceae in the phylum Ascomycota (Kirk 2011).

The genus *Bipolaris* (teleomorph: *Cochliobolus*) includes over 45 species that range from economically important pathogens of monocotyledonous hosts, such as wheat, barley, rice, and corn, to opportunistic human pathogens (Choudhry et al. 2010). On switchgrass, *B. oryzae, B. sorokiniana*, and *B. spicifera* have been described as pathogenic in the United States (Farr and Rossman 2011, Krupinsky et al. 2004). Various species of *Bipolaris* are known to be seedborne and in 2004, *B. spicifera* was reported on grass seed exported from the United States to Korea (Koo et al. 2004).

Species of the genus *Fusarium* (teleomorph: *Gibberella* spp., *Nectria* spp., *Calonectria* spp., and *Micronectria* spp.)

are a diverse array of mitosporic fungi, many of which are phytopathogenic to a wide range of plants under different environmental conditions (Booth 1971, Doohan et al. 2003). *Fusarium* species cause economically important diseases of monocotyledonous hosts such as *Fusarium* head blight of wheat and ear rot of corn (Parry et al. 1995, Sutton 1982). Some nonpathogenic *Fusarium* species are endophytic and can be added to soil to protect plants against fungal pathogens, including pathogenic species of *Fusarium* (Kavroulakis et al. 2007). *Fusarium* species have also been shown to have activity in *Fusarium* wilt-suppressive soils (Weller et al. 2002).

The genus *Curvularia* (teleomorph: *Cochliobolus*) includes species pathogenic to a wide range of hosts including wheat, rice, yam, mango, citrus, coconut and sorghum (de Luna et al. 2002). *Curvularia* spp. can be seedborne or soilborne and can cause primary infections, secondary infections, and post-harvest diseases (Lockwood 1988, Meehan 1947, Ray and Raavi 2005). *Curvularia lunata* has been found on grass seed exported from the United States to Korea (Koo et al. 2004) and *C. geniculata* has been identified causing secondary leaf spot on switchgrass in Kansas and Nebraska (Anonymous 1960).

In addition to their potential for decreasing crop yields, pathogens of switchgrass also are being investigated for use in the degradation of plant material in the conversion process of plant biomass to ethanol (Gibson et al. 2011). Plant pathogens may be pre-adapted for this new use as they have evolved numerous ways to degrade plant cell walls. Research is currently being conducted to exploit these mechanisms and enzymes for use in lignocellulose digestion of second-generation biofuels crops such as switchgrass.

During the conversion process from cellulose to ethanol, the switchgrass biomass undergoes a series of biochemical reactions during which the switchgrass extractives are inhibitory to the process (Thammasouk et al. 1997). The ethanol-soluble switchgrass extractives contain phenolic compounds such as p-coumaric, ferulic, and sinapic acids, which are associated with antimicrobial activity, antioxidant activity, UV protection, and the induction of the systemic resistance response that plants exhibit in the presence of pathogens (Chen et al. 2010, Graf 1992, Herald and Davidson 1983, Kikuzaki et al. 2002, Nicholson and Hammerschmidt 1992, Walker 1994). In humans and mice, these phenolic compounds have also been shown to have anti-inflammatory activity, cholesterol-lowering capacity, and the ability to boost natural immune defenses (Chawla et al. 1987, Hu et al. 1990, Liu 1987).

Phenolic compounds can prevent plant diseases by inducing plant defense responses or by preventing pathogen growth (Nicholson and Hammerschmidt 1992). The responses of plants to pathogens have been differentiated based on host and non-host interactions, both of which are characterized by the early accumulation of phenolic compounds at the infection site (Fernandez and Heath 1989, Heath 1980). Commercial products are available that use plant extractives to induce resistance against both bacterial and fungal plant pathogens (Marrone BioInnovations 2009, Randoux et al. 2006). These products can be used in both conventional and organic crop production. For instance, Randoux et al. (2006) used giant-knotweed extract to inhibit fungal growth and enhance plant defenses in wheat inoculated with *Blumeria graminis* f. sp. *tritici* (Randoux et al 2006).

Switchgrass (*Panicum virgatum* L.) is a perennial grass currently being investigated for use as a biomass feedstock for cellulosic ethanol production. Switchgrass biofuel has a low production cost and yields much more renewable energy than nonrenewable energy consumed in the process of production. Also, estimated greenhouse gas emissions from switchgrass-derived ethanol are 94% lower than estimated greenhouse gas emissions from gasoline (Schmer et al. 2008).

Although switchgrass-derived cellulosic ethanol production is a main focus of the biofuels initiative in Tennessee, only limited research has been done on pathogens that occur on switchgrass grown in the state. As expansive monocultures of switchgrass are developed for commercial production, disease pressure is likely to increase due to lack of plant biodiversity in those fields.

Previous studies have shown that nearly 150 species of fungi occur on switchgrass; with 75 confirmed pathogens in the United States (Fan and Rossman 2011). Prior to this study, only one fungal disease had been reported in Tennessee: rust caused by *Puccinia emaculata* (Zale et al. 2008). The lack of reports of switchgrass pathogens in Tennessee does not indicate a lack of presence. In 2008, researchers at the University of Tennessee found *Tilletia pulcherrima* (causal agent of bunt disease) on switchgrass seed that had been produced in Texas and distributed to growers in Tennessee (Carris et al. 2008). The purpose of this research was to develop information on fungal pathogens that decrease crop yield and quality of switchgrass grown in Tennessee.

Switchgrass (*Panicum virgatum* L.) is a warm-season grass that, due to its ability to adapt to a wide variety of environmental conditions, low fertility requirements, and low production cost, is being grown for biofuel production across the US and around the world. Although switchgrass is a perennial plant, stand establishment has proven to be a problem for growers. One factor contributing to the problem of stand establishment is poor seed quality (Parrish and Fike 2005; Sanderson et al. 2006). To our knowledge, only two studies have been conducted to examine switchgrass seed for pathogens (Carris et al. 2008, Tomaso-Peterson and Balbalian 2010).

In our studies, we have observed increased stand establishment and enhanced growth and vigor with surface-sterilized seed versus untreated seed (unpublished data). Currently, no seed certification program exists for switchgrass. The objective of this study was to identify major seedborne pathogens, their incidence in diverse seed lots, and the current geographic distribution of these organisms as determined by seed source location.

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

FIG. 1A: Conidia of *Alternaria alternata*; FIG. 1B: Acropetal conidial ontogeny with branching of *A. alternata*.

FIG. 4A. Conidiophores with conidia of *Bipolaris spicifera*; FIG. 4B. Bipolar germination of *B. spicifera*.

FIG. 7A: Colony morphology of *Fusarium pseudograminearum* on potato dextrose agar; FIG. 7B: Conidia of *F. pseudograminearum*.

FIG. 9A: Colony morphology of *S. homoeocarpa* on potato dextrose agar; FIGS. 9B-9C: Disease lesions caused by *Sclerotinia homoeocarpa* on switchgrass.

Figure 1:
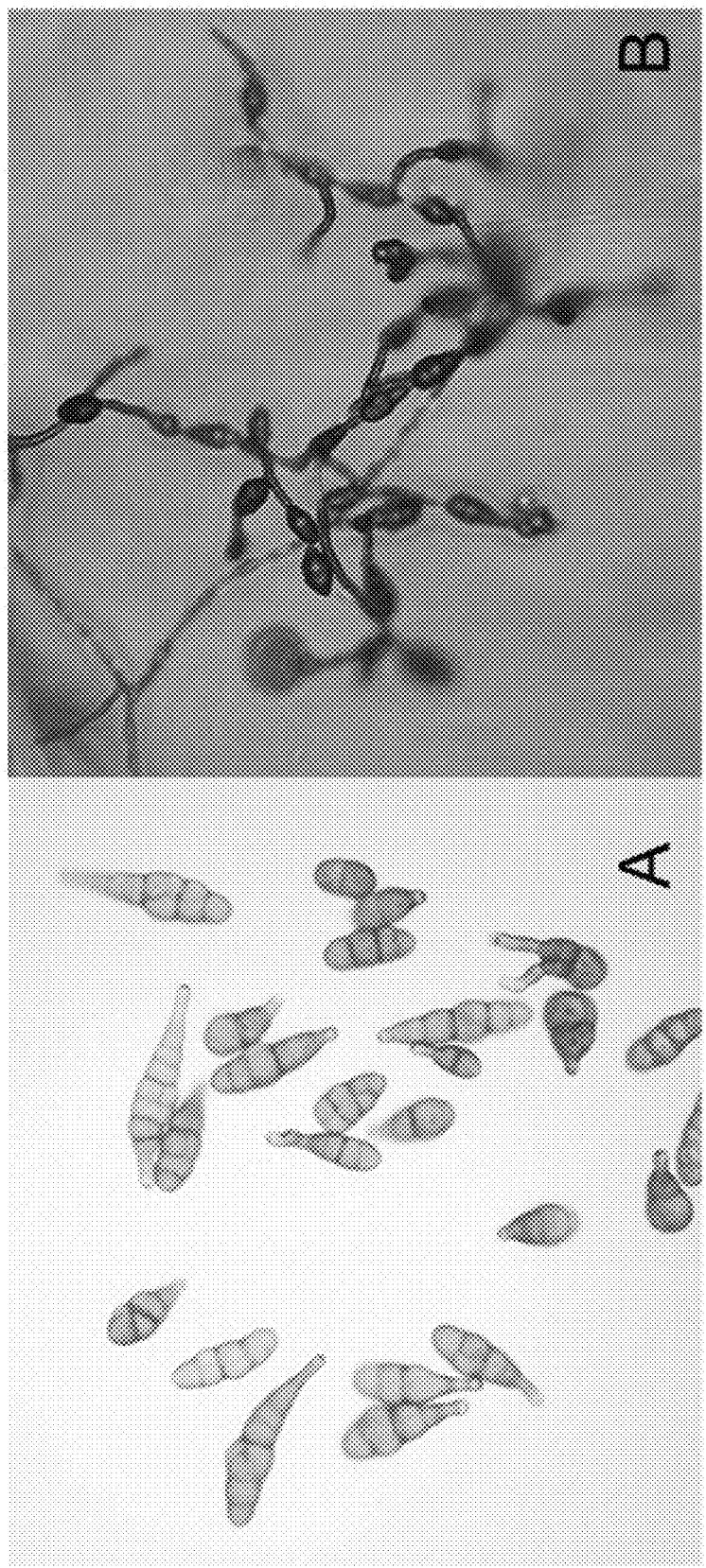
FIGS. 1A-1B.

DETAILED DISCLOSURE OF THE INVENTION

The specific objectives of this study were: 1) to identify fungal pathogens that occur naturally on seedlings and mature switchgrass plants grown in Tennessee; 2) to identify seedborne pathogens of switchgrass; 3) to determine the antimicrobial potential of switchgrass extractives.

Switchgrass (*Panicum virgatum* L.) is a perennial warm-season ($C_4$) prairie grass that is native to many regions of the United States. Switchgrass is being investigated as a lignocellulose feedstock crop due to its wide adaptability and perennial growth characteristics, but the process of breaking down switchgrass plant material to fermentable sugars is still being optimized. Several systems have been developed that use mechanical/chemical disruption to breakdown complex sugars to simpler sugars through a pretreatment step prior to saccharification and fermentation (Tao et al. 2011). Saccharification and fermentation employ a battery of microorganisms for sugar breakdown and conversion (Keshwani and Cheng 2009). When switchgrass plant material is ground and extracted with polar solvents, extractives (low molecular-weight lipophilic and hydrophilic compounds) are released into solution, leaving behind desired carbohydrates. Ethanol-soluble extractives contain various fatty acids, fatty alcohols, glycerol, alkanes, and sterols (Yan et al. 2010). When plant material is extracted with hot water, composition of extractives is similar to that of the ethanol-soluble extractives (Thammasouk et al. 1997). Hot water extractives contain antioxidants, such as $\alpha$-tocopherol and policosanol (Ravindranath et al. 2009). Flavonoids, such as quercitrin and rutin, can be found in the compounds extracted with both hot water and methanol (Uppugundla et al. 2009). Water-soluble extractives from switchgrass were shown to be composed of 30 to 35% of a "red-brown" fraction, which in experiments with corn stover conducted by the same research laboratory contained phenolic compounds such as p-coumaric, ferulic, and sinapic acids (Chen et al. 2007, Chen et al. 2010). The solubility of these compounds into solution during saccharification and fermentation could potentially inhibit enzymatic and microbial activity, thereby, decreasing overall ethanol yields per gram of starting material. Removal of the extractives prior to the pretreatment step may increase overall conversion efficiency, and the extractives could be exploited for antimicrobial activity as a value-added product. In this study, total phenols were measured and the antimicrobial activity of switchgrass-derived extractives was tested against four bacterial plant pathogens: *Clavibacter michiganensis* subsp. *michiganensis, Xanthomonas perforans, Pseudomonas syringae* pv. *tomato*, and *Pseudomonas mediterranea.*

Switchgrass is a perennial warm-season native grass currently being investigated for use in biomass-based ethanol production in Tennessee. However, little is known about fungal diseases that occur, or the impact of these diseases on crop yield. Disease reduction could significantly increase biomass yield and overall crop quality, particularly in the southeastern U.S. where large monocultures are being planted. The goal of this project was to identify fungal pathogens of switchgrass to form a foundation for understanding of role of disease in the overall efficiency and sustainability of switchgrass as a biofuel crop. Naturally infected 'Alamo' switchgrass plants were collected from growers' fields in Vonore, Tenn. in summer 2009 and agronomic research plots and ornamental plantings in Knoxyille, Tenn. in winter 2007 through spring 2008, and again in summer 2010. Fungi were isolated from diseased plants and pathogenicity was confirmed with Koch's postulates in growth chamber studies with whole plant assays. Pathogenic species of *Alternaria, Bipolaris*, and *Fusarium* were identified; several of these species had not been described previously on switchgrass, but are known to reduce quality and yield of other monocotyledonous crops. Species identification was based on morphology of conidia and conidiogenous cells, colony characteristics, colony growth at various temperatures, and confirmed by comparison of internal transcribed spacer (ITS) and mitochondrial small subunit (SSU) sequences of ribosomal DNA with nucleotide sequences in the National Center for Biotechnology Information (NCBI) GenBank database.

Mature 'Alamo' switchgrass plants, with symptoms of leaf, stem, or root disease, were collected from agronomic research plots or ornamental plantings in Knoxyille, Tenn. in winter 2007 through spring 2008, and again in summer 2010. Naturally-infected switchgrass seedlings and mature plants also were collected from agronomic stands in Vonore, Tenn., in summer 2009. Plant tissue was surface-sterilized with 95% ethanol for 1 min, 20% commercial bleach ($NaClO_3$; Clorox, Oakland, Calif.) for 2 min, 95% ethanol for 1 min, dried on sterile filter paper, and plated on 2% water agar amended with 10 mg/liter rifampicin (Sigma-Aldrich, St. Louis, Mo.) and 5 to 10 μl/liter miticide (2.4 EC Danitol, Valent Chemical, Walnut Creek, Calif.). Fungal hyphae were transferred to potato dextrose agar (PDA) for axenic culture and identified based on morphology of conidia, conidiogenous cells, and colony growth. In some cases, isolates were grown on specialized culture media and were cultured at different incubation temperatures to determine identification.

Some fungi (*Alternaria alternate, Bipolaris sorokiniana, Pithomyces chartarum*) were isolated also from plants grown in growth chambers intended for pathogenicity studies, indicating that the isolated pathogen had been seedborne. 'Alamo' seed (Seedland, Wellborn, Fla.) had been surface-sterilized with 70% Clorox for 30 min, washed with sterile water, and dried prior to planting. Organisms were isolated and identified as described for pathogens from diseased tissues. All seed planted for subsequent pathogenicity tests were scarified with 60% sulfuric acid then surface-sterilized with 50% Clorox for 30 min, washed with sterile water, and shaken in sterile water for 1 to 3 days prior to planting (Gwinn et al. 1991).

For pathogenicity assays, seed were sown in 9×9-cm pots containing 50% ProMix Potting and Seeding Mix (Premier Tech Horticulture, Rivière-du-Loup, Québec, Canada) and 50% Turface ProLeague (Profile Products, Buffalo Grove, Ill.) (v/v). A conidial spore suspension ($10^4$ to $10^7$ spores/ml water) or mycelial slurry was made from each fungus and sprayed on 6 to 10 replicates of switchgrass seedlings in a growth chamber. Plants were kept at high humidity for 2 to 7 days at 25/20° C. with a 12-hour photoperiod. Symptomatic plant tissue was collected. Fungi were re-isolated and identified as described above to fulfill Koch's postulates.

Genomic DNA was extracted from each isolate and re-isolate (obtained from the Koch's postulates pathogenicity assay) with the DNeasy Plant Mini Kit (Qiagen, Valencia, Calif.). Ribosomal DNA from the internal transcribed spacer (ITS) region was amplified with polymerase chain reaction (PCR) with primers ITS4 and ITS5 (White et al. 1990). The DNA fragments were sequenced and checked against the GenBank database with BLASTn (NCBI). For cases in which the ITS sequence was not specific enough for an exact GenBank match, DNA from an internal region of the mitochondrial small subunit (SSU) gene was amplified with PCR with primers NMS1 and NMS2 (Li et al. 1994). DNA fragments were sequenced and checked against the GenBank database with BLASTn (NCBI).

*Alternaria alternata* (Fries) Keissler

'Alamo' switchgrass grown in Vonore, Tenn. was found exhibiting light brown-to-dark brown spots and general chlorosis in June, 2009. Symptomatic leaf tissue samples were surface-sterilized and plated on 2% water agar amended with antibiotic and miticide as described earlier. Plates were incubated at 26° C. for 4 days in darkness. An asexual, dematiaceous mitosporic fungus was isolated and transferred to PDA. Cultures were transferred to *Alternaria* sporulation medium (Shahin and Shephard 1979) to induce conidial production and to dichloran rose bengal yeast extract sucrose agar to determine morphological features and colony growth characteristics (Andersen et al. 2001, Simmons 1999). Pathogenicity studies were conducted with nine pots of approximately 20 plants each of 5-week-old 'Alamo' switchgrass plants grown from surface-sterilized seed. Plants were wounded by trimming the tops to a height of approximately 5 cm. Eight pots were sprayed with a conidial spore suspension of $5.07 \times 10^6$ spores/ml sterile water and subjected to high humidity by enclosure in a plastic bag for 7 days. One pot was sprayed with sterile water and subjected to the same conditions to serve as a control. Plants were maintained in a growth chamber at 25/20° C. with a 12-h photoperiod. Lesions were excised, surface-sterilized, plated on water agar, and identified in the same manner as previously described. The ITS region of ribosomal DNA and the mitochondrial SSU region from the original isolate and the re-isolate recovered from the pathogenicity assay were amplified with PCR, with primers ITS4 and ITS5 and NMS1 and NMS2, respectively.

*Bipolaris oryzae* (Breda de Haan) Shoemaker 1959

Dark brown to black irregular-shaped foliar spots were observed on 'Alamo' switchgrass grown on the campus of the University of Tennessee in December 2007. Symptomatic leaf tissue samples were surface-sterilized and plated on 2% water agar amended with antibiotic and miticide as described earlier. An asexual, sparsely-sporulating, dematiaceous mitosporic fungus was observed and fungal plugs were transferred to surface-sterilized detached leaves on sterile filter paper in a moist chamber to increase spore production. Disease assays were conducted with 6-week-old switchgrass plants grown from seed scarified with 60% sulfuric acid and surface-sterilized in 50% bleach (Gwinn et al. 1991). Nine pots with approximately 20 plants per pot were inoculated with a mycelial slurry. Two additional pots were inoculated with sterile water and subjected to the same conditions to serve as a control. Plants were subjected to high humidity by enclosure in a plastic bag for 72 h. Bags were removed and plants were incubated at 25/20° C. with 50 to 60% relative humidity. During the incubation period, plants were maintained in a growth chamber with a 12-h photoperiod of fluorescent and incandescent lighting. Symptomatic leaf tissue was processed and plated as described above. The ITS region of ribosomal DNA from the original isolate and from the isolate recovered from plants in the pathogenicity assay was amplified with PCR, with primer pairs ITS4 and ITS5.

*Bipolaris sorokiniana* (Saccardo) Shoemaker

Light to dark brown, irregular-shaped leaf spots, chlorosis, necrotic roots, and severe stunting were observed on 'Alamo' switchgrass grown on the campus of the University of Tennessee in December 2007. Symptomatic leaf and root samples were surface-sterilized and plated onto water agar amended with antibiotic and miticide as described earlier. Plates were incubated at 25° C. in darkness for 4 days. A sporulating, dematiaceous mitosporic fungus was noted and transferred to PDA. Disease assays were conducted with 5-week-old 'Alamo' switchgrass grown from surface-sterilized seed. Ten pots with approximately 20 seedlings were sprayed with $2.4 \times 10^5$ spores/ml of sterile water, with one control plant sprayed with sterile water and subjected to the same conditions as treated plants. Plants were subjected to high humidity created by enclosure in a plastic bag for 45 h. The bag was removed and plants were incubated at 25/20° C. with 50 to 60% relative humidity. During the incubation, plants were maintained in a growth chamber with a 12-h photoperiod of fluorescent and incandescent lighting. Foliar lesions and diseased roots were surface-sterilized, plated on water agar, and the resultant fungal colonies were processed as described earlier. The ITS and mitochondrial SSU regions of ribosomal DNA from the original isolate, and the isolate recovered from plants in the pathogenicity assay, were amplified with PCR, with primer pairs ITS4 and ITS5, and NMS1 and NMS2, respectively.

*Bipolaris spicifera* (Bainier) Subramanian

Light to dark brown leaf spots and general chlorosis were observed on 'Alamo' switchgrass grown in ornamental plantings on the campus of the University of Tennessee in Knoxville in December 2007. Disease distribution was patchy, infecting approximately 10% of plants. Patches had mild to severely infected plants, with stunting in areas of severe infection. Symptomatic leaf tissue was surface-sterilized and plated onto water agar amended with antibiotic and miticide as described earlier. Plates were incubated at 26° C. in darkness for 5 days. A sporulating, dematiaceous mitosporic fungus was observed and transferred to PDA. Pathogenicity studies were conducted with 5-week-old 'Alamo' switchgrass plants grown from surface-sterilized seed. Ten replicate pots with approximately 20 plants each were sprayed with a spore suspension of $4.5 \times 10^6$ spores/ml of sterile water prepared from 6-day-old cultures grown on PDA. Plants were subjected to high humidity for 45 h by enclosure in a plastic bag, and then incubated at 25/20° C. with a 12-h photoperiod in a growth chamber. Two control pots were inoculated with sterile water and subjected to the same conditions. Lesions were excised from leaves, surface-sterilized, plated on water agar for morphological identification. The ITS region of ribosomal DNA from the original isolate used for inoculation and the re-isolated culture recovered from plants in the pathogenicity studies were amplified with PCR using primers ITS4 and ITS5 (White 1990).

*Fusarium acuminatum* Ellis & Everhart

In June 2009, 'Alamo' switchgrass leaf and stem samples with brown leaf spots and streaks were collected from agronomic switchgrass plots in Vonore, Tenn. Infected tissue was surface-sterilized and plated on 2% water agar amended antibiotic and miticide as described earlier. Plates were incubated for two days at 22.5° C., and the fungus was transferred to PDA. Cultures were incubated at 22.5° C. in the dark for 5-7 days and on carnation leaf agar (CLA) for further identification. Morphological identification was enhanced by incubating cultures on PDA at 25° C. with no light, 30° C. with light, and alternating between 25° with light for 12 h and 20° C. in darkness for 12 h. Pathogenicity was determined by inoculation of ten pots containing approximately 20 healthy switchgrass plants grown from surface-sterilized seeds. Leaves were wounded by trimming the tops and sprayed with $1.1 \times 10^6$ spores/ml water with an atomizer. Conidial solution was also sprayed on the crown of the plants at the soil surface. Two untreated pots were sprayed with sterile water to serve as controls. Plants were subjected to high humidity by enclosure in a plastic bag. Bags were removed after 24 h and plants were incubated at 27° C. in a growth chamber. The ITS region of ribosomal DNA and mitochondrial SSU DNA from the original isolate and the re-isolated culture were amplified with PCR using primers ITS4 and ITS5, and NMS1 and NMS2, respectively.

*Fusarium equiseti* (Corda) Saccardo

Light brown to brown leaf spots, general chlorosis, and stunting were observed on 'Alamo' switchgrass grown on the campus of the University of Tennessee in December 2007. Infected root and crown tissue was surface-sterilized and plated on 2% water agar amended with antibiotic and miticide as described earlier. Plates were incubated for two days at 22.5° C. and emergent fungal growth was transferred to PDA. Cultures were incubated in darkness at 22.5° C. on PDA and on CLA for identification. Pathogenicity was determined by inoculation of nine pots containing approximately 20 healthy switchgrass plants grown from surface-sterilized seeds. Leaves were wounded by trimming the tops to a height of approximate 5 cm and roots were wounded with a sterile surgical blade, and then sprayed with $4.7 \times 10^6$ spores/ml water with an atomizer on and around the crown of the plant at the soil surface. Two control pots were sprayed with sterile water to serve as controls. Plants were subjected to high humidity by enclosure in a plastic bag. Bags were removed after 48 h and plants were incubated at 27° C. in a growth chamber. The pathogen was re-isolated from symptomatic leaf and root tissue and identified on PDA based on spore morphology as described above. The ITS region of ribosomal DNA from the original isolate and the re-isolate was amplified with PCR using primers ITS4 and ITS5.

*Fusarium pseudograminearum* Aoki & O'Donnell

In June 2009, 'Alamo' switchgrass leaf and stem samples showing brown leaf spots and streaks were collected from agronomic switchgrass plots in Vonore, Tenn. Infected stem tissue was surface-sterilized and plated on 2% water agar amended with antibiotic and miticide as described earlier. Plates were incubated for 2 days at 22.5° C. The resultant fungus was transferred to PDA and CLA for morphological identification.

Pathogenicity was determined by inoculation of eight pots containing approximately 20 healthy switchgrass plants grown from surface-sterilized seeds. Leaves were wounded by trimming the tops to a height of 5 cm, and then sprayed with $3.2 \times 10^5$ spores/ml water with an atomizer. Conidial solution was sprayed also on the crown of the plants at the soil surface. Two pots of plants were sprayed with sterile water to serve as controls. Plants were subjected to high humidity by enclosure in a plastic bag. Bags were removed after 48 h and plants were incubated at 26° C. in a growth chamber. The ITS region of ribosomal DNA from the original isolate and re-isolate recovered from plants in the pathogenicity studies were amplified with PCR using primers ITS4 and ITS5.

*Pithomyces chartarum* (Berkeley & M. A. Curtis) M. B. Ellis

Light brown to white bleached spots were observed on 'Alamo' switchgrass grown from surface-disinfested seed grown in Colorado in fall 2009. Symptomatic leaf tissue was surface-sterilized, air-dried on sterile filter paper, and plated on 2% water agar amended with antibiotic and miticide as described earlier. Plates were incubated at 26° C. in darkness for 5 days. A sporulating, dematiaceous mitosporic fungus was observed and transferred to PDA. Pathogenicity studies were conducted with 5-week-old 'Alamo' switchgrass plants grown from seed scarified with 60% sulfuric acid and surface-sterilized with 50% bleach. Eight replicate pots with approximately 20 plants each were sprayed with a spore suspension of $5.7 \times 10^5$ spores/ml of sterile water prepared from 6-day-old cultures grown on V8 juice agar in the dark. Plants were subjected to high humidity for 72 h by enclosure in a plastic bag, and then incubated at 25/20° C. with a 12-h photoperiod in a growth chamber. Lesions were excised from leaves, surface-sterilized, plated on water agar, and the resulting cultures were grown on PDA for morphological identification. The ITS region of ribosomal DNA from the original isolate and re-isolate were amplified with PCR using primers ITS4 and ITS5.

*Sclerotinia homoeocarpa* F. T. Bennett

*Sclerotinia homoeocarpa* causes dollar spot on many grass species; however it has not been described on switchgrass as a host. In August 2010, bleached, tan to straw-colored leaf spots with dark brown to reddish-brown margins were found in patchy distribution in small field plots of 'Alamo' switchgrass at the East Tennessee Research and Education Center, Knoxyille, Tenn. The plots had been planted to switchgrass for the past 21 years. Disease lesions covered 75-80% of leaf tissue per patch and were also evident on stems. To identify the pathogen, center portions of diseased leaves were cut into 20- to 30-cm-long segments, and surface-disinfested, then 5-cm-long sections that included a leading edge of a lesion were plated on PDA. Plates were incubated at 22° C.

Pathogenicity studies were conducted with 6-week-old 'Alamo' switchgrass grown from scarified and surface-disinfested seed (Gwinn et al. 1991). Nine pots with 18 plants each were inoculated with 20 mycelial plugs (6-mm-diameter) per pot, taken from 3-to-5-day-old fungal cultures. Two control pots were inoculated with sterile PDA plugs and subjected to the same conditions. Plugs were placed on leaf surfaces and around plant crowns. Plants were subjected to high humidity by enclosure in a plastic bag and incubated in a growth chamber at 25/20° C. with a 12-h photoperiod. Plastic bags were removed after 48 h. The fungus was cultured from leaf spots and stem lesions of inoculated plants as described above. The same disease and fungus were observed, completing Koch's postulates. The ITS region of ribosomal DNA from the original isolate and re-isolate was amplified with PCR, with primers ITS4 and ITS5. The mitochondrial SSU was amplified from the original isolate with primers NMS1 and NMS2.

*Alternaria alternata* (Fries) Keissler

Club-shaped conidia were produced in chains, with branching of chains present on *Alternaria* sporulation medium (FIG. 1). Conidia were 27 to 50 μm in length×10 to 15 μm in width (mean 42.5×12.5 μm). Morphological features and growth on dichloran rose bengal yeast extract sucrose agar were consistent with the characteristics described previously for *A. alternata* (Fr.) Keissl. (Andersen et al. 2001, Simmons 1999).

Foliar leaf spot symptoms appeared 5 to 10 days post-inoculation for all pots inoculated with *A. alternata* in the pathogenicity assay. Symptoms of *A. alternata* infection were not observed on the control. The ITS region sequences of the original isolate and the re-isolate were approximately 537 bp and were submitted to GenBank (Accession Nos. HQ130485.1 and HQ130486.1). The BLAST search (BLASTn, NCBI) against GenBank isolates indicated a match of 100% maximum identity with eight *A. alternata* isolates, including GenBank Accession No. AB470838. The SSU sequences were approximately 551 bp and matched 100% maximum identity for seven *A. alternata* isolates, including GenBank Accession No. AF229648. *Alternaria alternata* has been reported from switchgrass in Iowa (Gravert and Munkvold 2002); however, pathogenicity was not confirmed with Koch's postulates in that report. To our knowledge, this is the first report of *A. alternata* causing leaf spot on switchgrass in Tennessee.

*Bipolaris oryzae* (Breda de Haan) Shoemaker 1959

Figure 2:
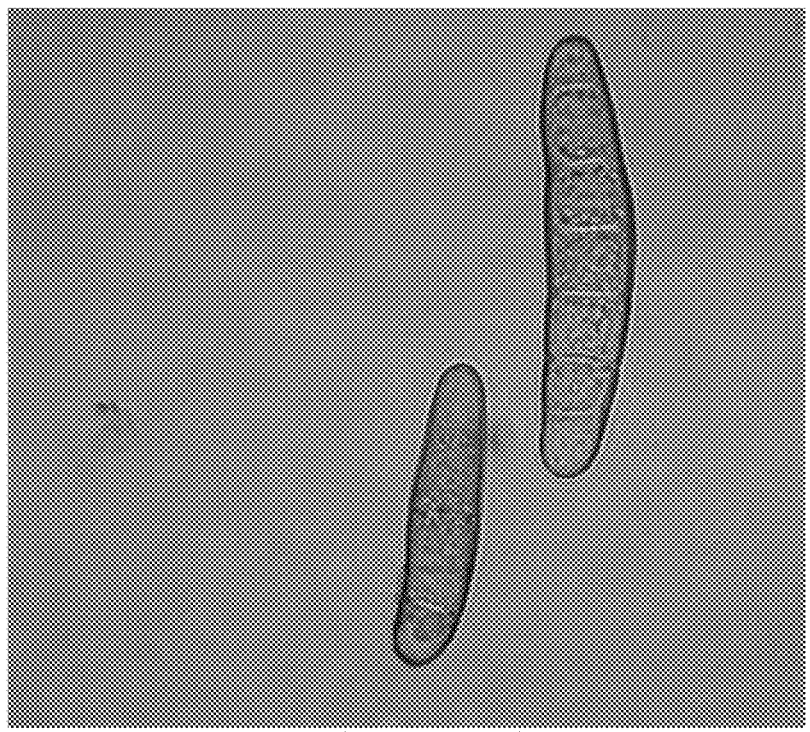
FIG. 2. Conidia of *Bipolaris oryzae*.

Conidia were ovate, oblong, mostly straight to slightly curved, and light to olive-brown with three to ten septa (FIG. 2). Conidial dimensions were 12.5×27.5 to 17×95 (average 14.5×72) µm. Conidia were produced on single, light brown, multiseptate conidiophores that were polytretic, geniculate, and sympodial. Morphological characteristics and disease symptoms were similar to those described for *B. oryzae* (Breda de Haan) Shoemaker (Sivanesan 1987, Krupinsky et al. 2004).

In the pathogenicity assay, foliar leaf spot symptoms appeared 5 to 14 days post-inoculation for eight of nine replicates. Control plants showed no symptoms. PCR amplicons of the ITS region were approximately 534 bp. Amplicon sequences from the original isolate and re-isolate were identical and had 99% homology to several *B. oryzae* isolates from switchgrass in Mississippi (GenBank Accession Nos. GU222690, GU222691, GU222692). Leaf spot caused by *B. oryzae* on switchgrass has been described in North Dakota, Mississippi, and New York (Farr and Rossman 2011) and the fungus has been shown to have seedborne transmission (Tomaso-Peterson and Balbalian 2010).

*Bipolaris sorokiniana* (Saccardo) Shoemaker

Figure 3:
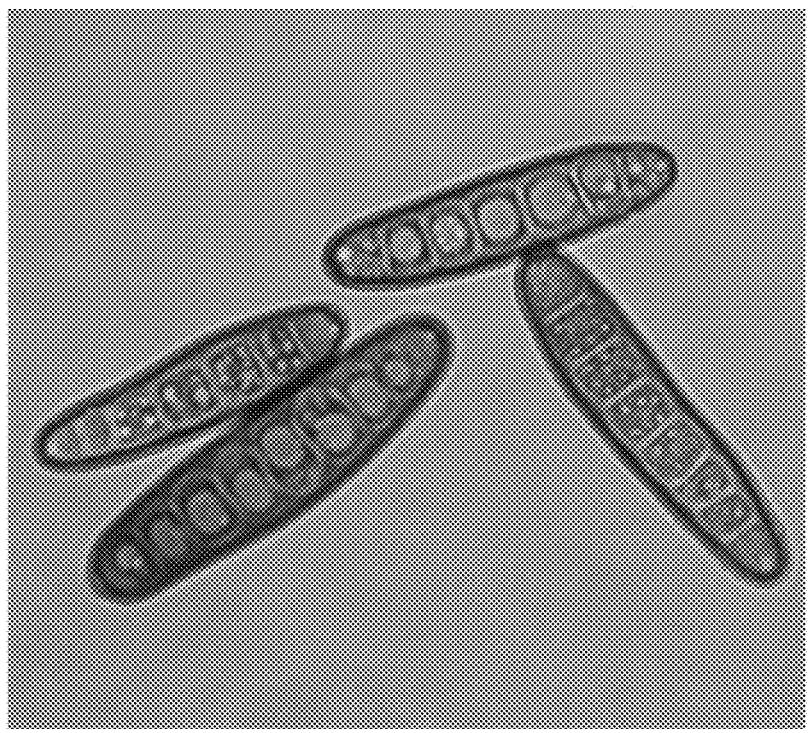
FIG. 3. Conidia of *Bipolaris sorokiniana*.

On PDA, conidia were ovate, oblong, mostly straight, and olive to brown with three to nine septa (FIG. 3). Conidial dimensions were 12.5×27.5 (17.5) to 20×77.5 (57) µm. Conidia were produced on single, light brown, multiseptate conidiophores that were polytretic, geniculate, and sympodial. Morphological features were as described for *B. sorokiniana* (Sacc.) Shoemaker (teleomorph=*Cochliobolus sativus*) (Nyvall and Percich 1999, Sivanesan and Holliday 1981).

In the pathogenicity assay, foliar leaf spot symptoms appeared 6 to 10 days post-inoculation for plants in all 10 replicates and necrotic lesions were observed on roots. Resultant colonies were identified as *B. sorokiniana*.

PCR amplicons of the ITS and SSU regions of approximately 551 and 571 bp were obtained, respectively. Both amplicons were obtained from each isolate and sequenced. Amplicon sequences from the original isolate and re-isolate were identical and the sequences were submitted to GenBank (Accession Nos. HQ611957 and HQ611958). The ITS sequences had 98% homology to 23 *B. sorokiniana* isolates, including *B. sorokiniana* strain DSM 62608 (GenBank Accession No. EF187908); SSU sequences had 99% homology to *Cochliobolus sativus* isolate AFTOL-ID 271 (GenBank Accession No. FJ190589).

Spot blotch caused by *B. sorokiniana* has been reported on switchgrass in Iowa, Nebraska, Pennsylvania, and Virginia (Fan and Rossman 2010). To our knowledge, this is the first report of *B. sorokiniana* causing spot blotch or common root rot of switchgrass in Tennessee, which extends the current known distribution of these diseases. *Bipolaris sorokiniana* was isolated also from switchgrass seed received from commercial sources in the United States, indicating seedborne transmission.

*Bipolaris spicifera* (Bainier) Subramanian

Figure 4:
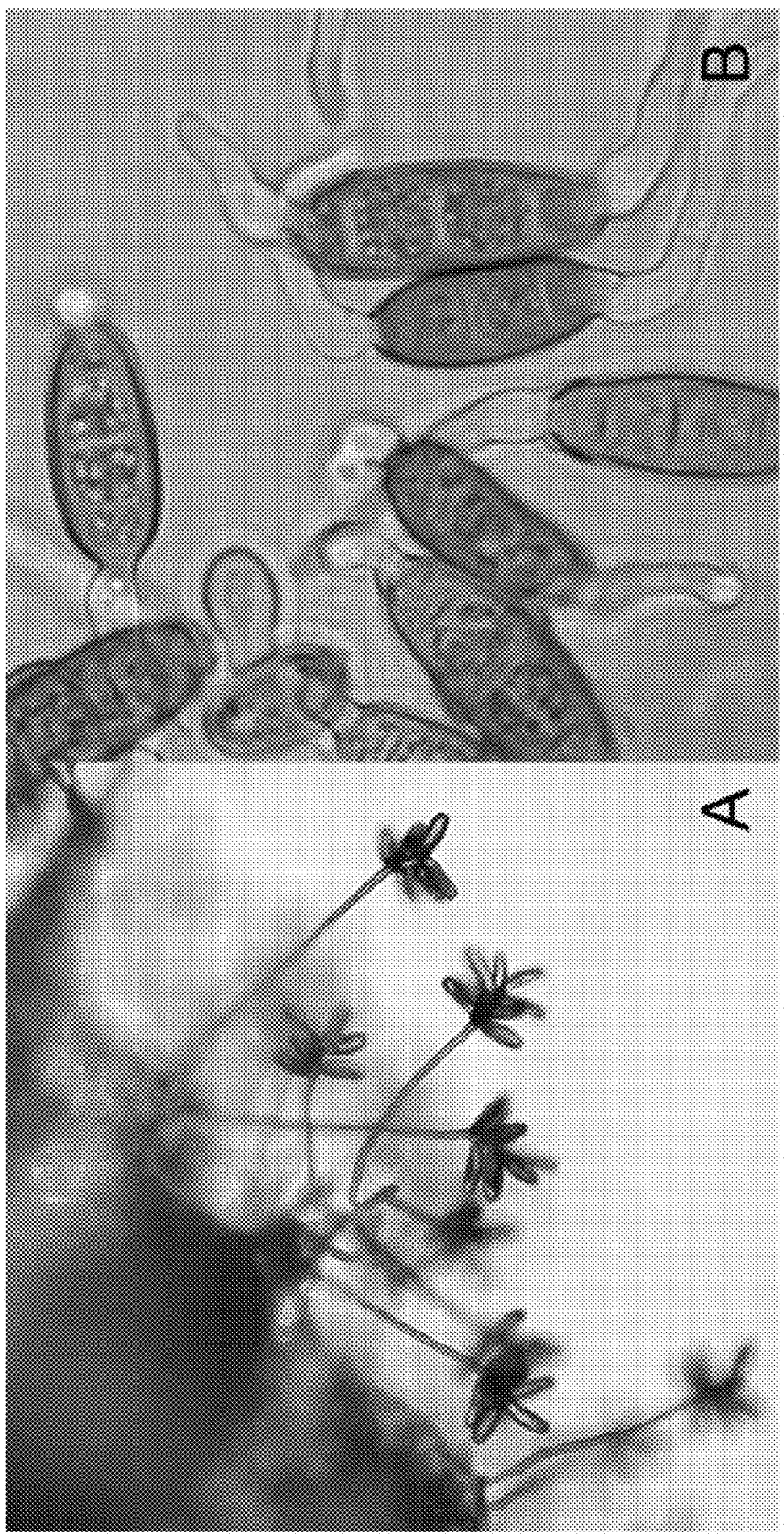
FIGS. 4A-4B.

Conidiophores were single, light brown, multiseptate, mostly straight, polytretic, geniculate, and sympodial (FIG. 4A). Conidia were 17.5×12 µm to 30×14 µm (mean 22×12.5), oval, light brown, and distoseptate, with one to three septa and a flattened hilum on the basal cell. Conidia germinated from both poles (FIG. 4B). The causal agent was identified as *B. spicifera* (Bainier) Subram. Morphological features were as described for *B. spicifera* (Koo et al. 2003). Leaf spot symptoms similar to the original disease appeared on plants in each of the 10 inoculated replicate pots 6 days post-inoculation in the pathogenicity assay. These symptoms were not observed in the control pots. The re-isolate was also identified as *B. spicifera*. PCR amplicons of ~560 bp were obtained from both isolates and sequenced. Amplicon sequences were identical and the sequence was submitted to GenBank (Accession No. HQ015445). The DNA sequence had 100% homology to the ITS sequence of *B. spicifera* strain NRRL 47508 (GenBank Accession No. GU183125.1) that had been isolated from sorghum seed. To our knowledge, leaf spot caused by *B. spicifera* has not been described on switchgrass (Farr and Rossman 2011). *Bipolaris spicifera* can be seedborne and has been reported on turfgrass seed exported from the United States to Korea (Koo et al. 2003).

*Fusarium acuminatum* Ellis & Everhart

Figure 5:
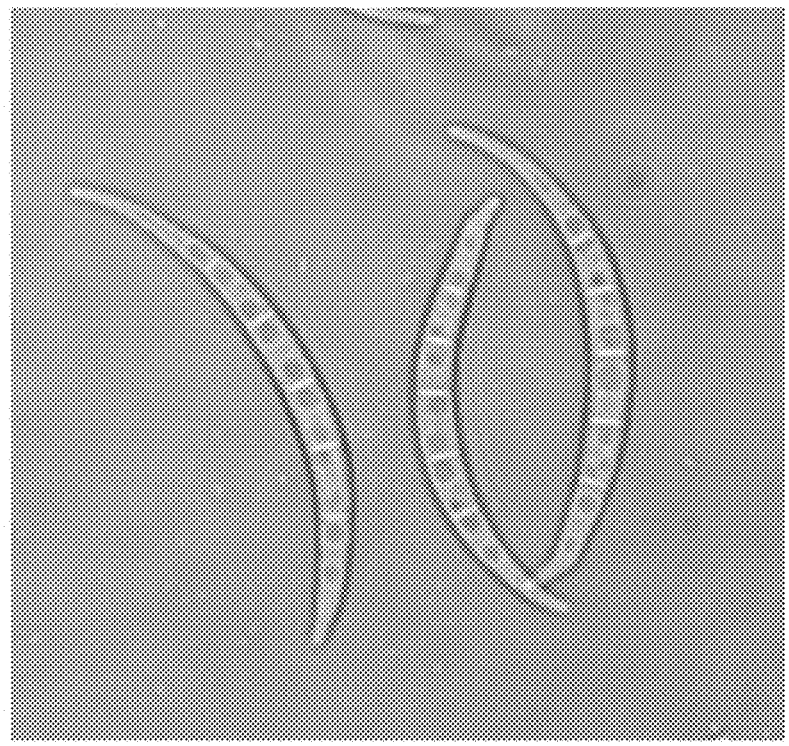
FIG. 5. Conidia of *Fusarium acuminatum*.

Cultures on PDA, incubated at 22.5° C. in the dark for 5-7 days, produced white to light yellow-orange, fluffy, aerial mycelium with sporulation. The culture was light yellow as viewed from the reverse of the culture plate. This fungus was identified as a species of *Fusarium*. After 5 days, the average colony size on PDA at 25° C. in darkness was 4.5×4.2 cm; at 30° C. with light, colony diameter was 5.2×4.9 cm; and at 25° C. with light/20° dark conditions, the colony diameter was 5.2×4.8 cm. Culture color under these conditions was white to light orange-yellow. Sporodochia on CLA were light orange and spores had a foot-shaped basal cell with a slightly elongated apical cell. Spores on PDA were hyaline and boat-shaped with 3 to 5 transverse septations, with spore size ranging from 45-88 µm in length×2.5-3.75 µm in width (FIG. 5). Chlamydospores were present after 5 to 6 weeks on CLA and no microconidia production was observed. The fungus was identified as *Fusarium acuminatum* Ellis & Everhart (Nelson et al. 1983, Booth 1971).

Inoculated plants in the pathogenicity assay developed symptoms 3 to 7 days post-inoculation for all ten replicates. Control plants had no symptoms. *Fusarium acuminatum* was re-isolated from symptomatic tissue and identified as described above.

PCR amplicons of 512 bp for the SSU region and 565 bp for the ITS region were obtained from both isolates and sequenced. Amplicon sequences were identical for the original and re-isolate for both primer sets. The SSU DNA sequence had 99% homology to the SSU sequence of *Gibberella acuminata* (GenBank Accession No. U85550.1), the sexual stage of *Fusarium acuminatum*. The ITS DNA sequence had 99% homology to *Fusarium acuminatum* (GenBank Accession No. AB587001.1) and *Gibberella acuminata* (GenBank Accession No. U85533.1). To our knowledge, this is the first report of *F. acuminatum* on switchgrass in Tennessee, extending the known geographic range of the pathogen (Farr and Rossman 2011).

*Fusarium equiseti* (Corda) Saccardo

Figure 6:
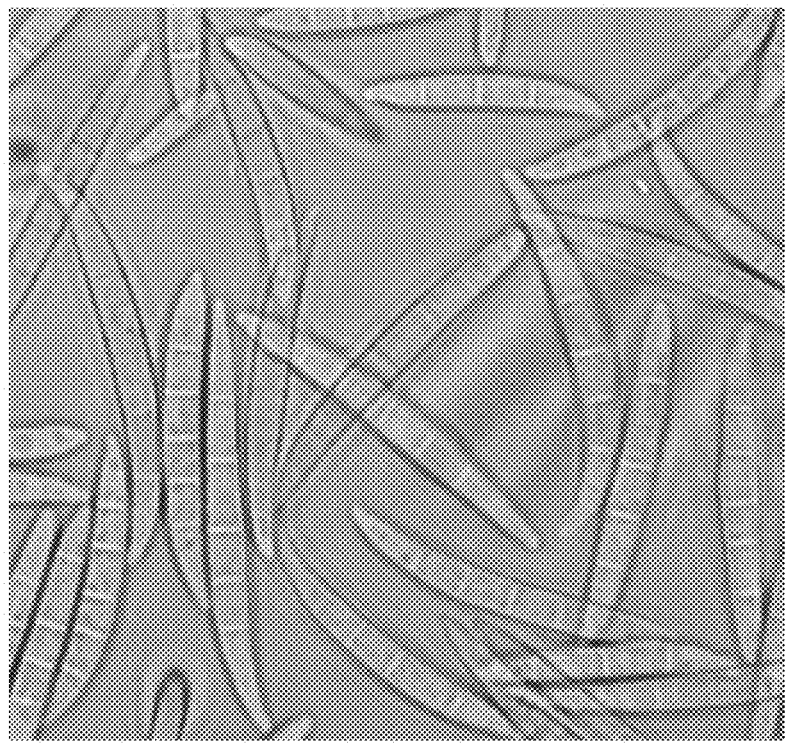
FIG. 6. Conidia of *Fusarium equiseti*.

Cultures incubated in darkness at 22.5° C. on PDA for 5-7 days had peach-to-light-orange, fluffy mycelium with profuse sporulation. The fungus was identified as a species of *Fusarium* and transferred to CLA to aid in species determination. Sporodochia on CLA were peach-colored and spores had a distinct foot-shaped basal cell with an elongated, tapered apical cell. Macroconidia were hyaline and boat-shaped with 4 to 7 transverse septations; spore size ranged from 27.5-88 µm in length×2.5-5 µm in width (FIG. 6). Chlamydospores were present after several weeks on CLA. The fungus was identified as *Fusarium equiseti* (Corda) Sacc. (Nelson et al. 1983, Booth 1971).

In the pathogenicity assay, inoculated plants showed symptoms after 3 to 9 days post-inoculation for all nine replicates. Control plants showed no symptoms. The re-isolate was identified as *F. equiseti* based on morphology.

The sequences of the PCR amplicons of ~512 bp obtained from both isolates were identical and had 100% homology to several *F. equiseti* isolates in GenBank, including isolate H02-765S (GenBank Accession No. EU595566), which had been isolated from sorghum, and isolate DH08023-2 (GenBank Accession No. GU073123), isolated from green foxtail. To our knowledge, this is the first report of *F. equiseti* infecting switchgrass in Tennessee (Farr and Rossman 2011).

*Fusarium pseudograminearum* Aoki & O'Donnell

Figure 7:
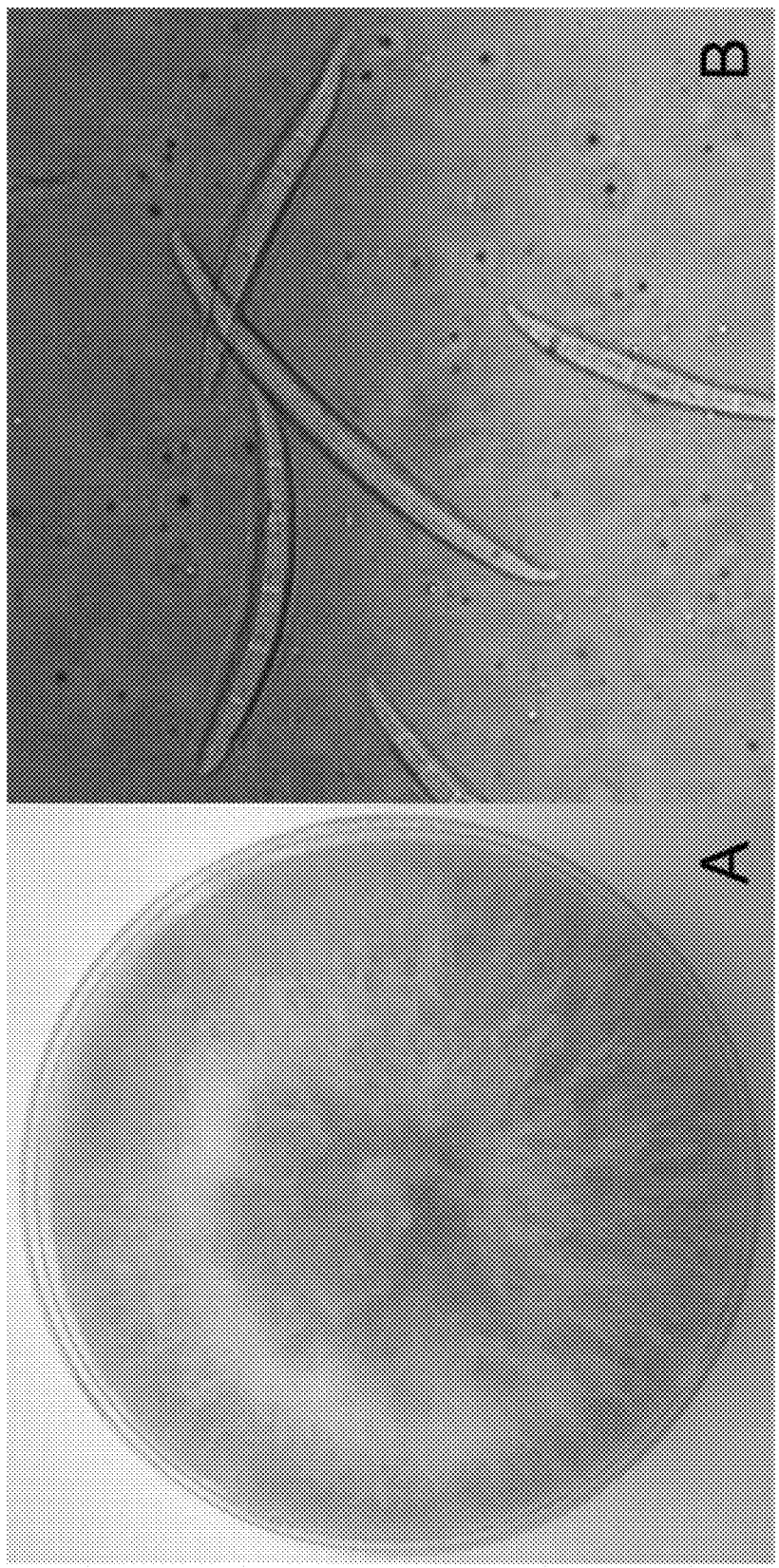
FIGS. 7A-7B.

After 5 to 7 days, the color of colonies grown on PDA and incubated at 22.5° C. in the dark ranged from a deep red to pink and orange, some with white aerial mycelium and some with flat growth and sporulation (FIG. 7A). Plates were vibrant pink when viewed from below. The fungus was identified as a species of *Fusarium* and transferred to CLA to aid in species determination. Spores on CLA had a foot-shaped basal cell with a tapered apical cell. Spores on PDA were hyaline, mostly straight to slightly curved with 4 to 6 transverse septations; spore size was 35-87 µm in length×3.5-6.75 µm in width (FIG. 7B). The fungus was identified as *F. pseudograminearum* Aoki & O'Donnell (Leslie and Summerell 2006).

Symptoms were evident in inoculated plants 5 to 9 days post-inoculation for all eight replicates. Control plants showed no symptoms. *Fusarium pseudograminearum* was re-isolated from symptomatic tissue and identified on PDA as described above.

PCR amplicons of the ITS regions of approximately 525 bp were obtained from both isolates and sequenced. Amplicon sequences were identical. The DNA sequence had 99% homology to the ITS sequences of many isolates listed as "*Fusarium* sp." DNA sequences had 99% homology also to isolates of *Fusarium graminearum*, which may be due to the fact that *F. pseudograminearum* was formerly classified as a subgroup of *F. graminearum*. Primary characteristics that differentiate these two species include disease symptomatology and whether reproduction of the isolate is hetero- or homothallic. *Fusarium graminearum* causes head blight and is heterothallic, while *F. pseudograminearm* causes crown rot and is homothallic. The isolate from switchgrass in this study was isolated from the host crown and stem. Further molecular and physiological analysis will be needed to confirm identification. To our knowledge, this is the first report of *F. pseudograminearum* causing disease on switchgrass as a pathogen, extending the known host range of the pathogen (Farr and Rossman 2011).

*Pithomyces chartarum* (Berkeley & M. A. Curtis) M. B. Ellis

Figure 8:
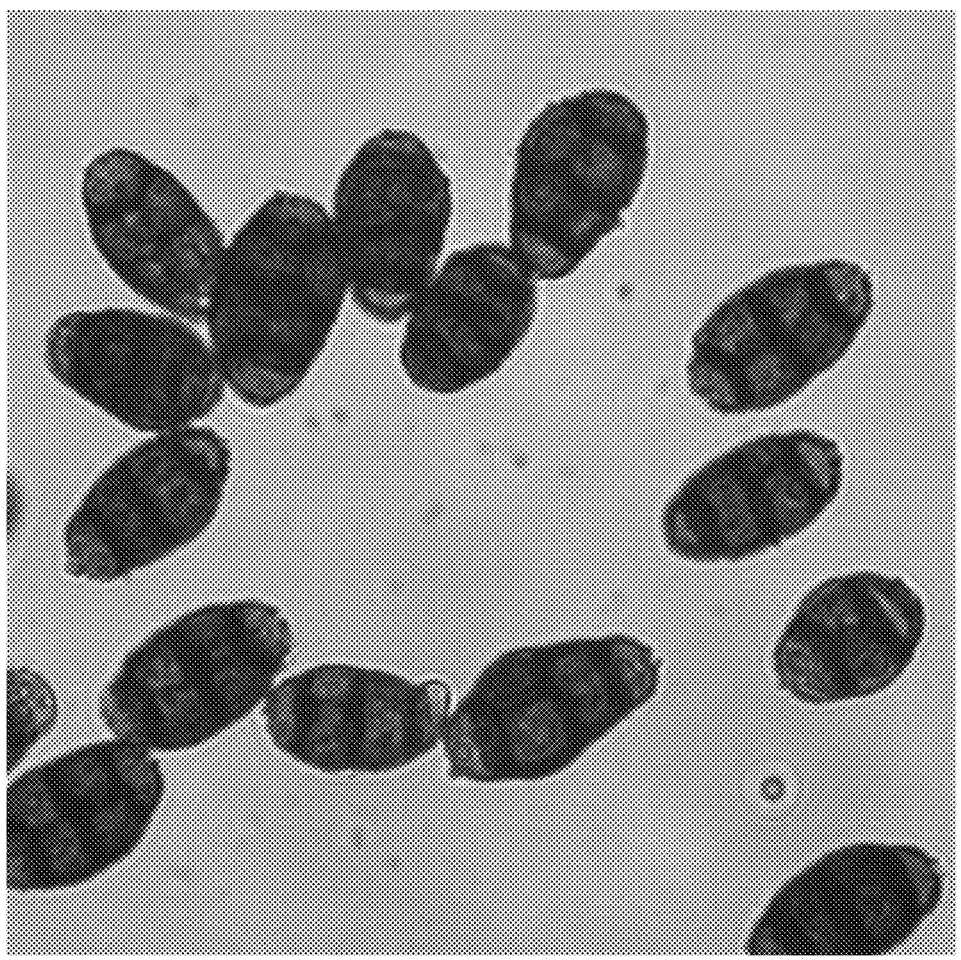
FIG. 8. Conidia of *Pithomyces chartarum*.

On PDA, incubated in darkness, conidia dimensions were 10-22.5 µm×20-37.5 µm (average 15.17×26.5), and were golden to dark brown, broadly ellipsoidal to some pyriform, with 2 to 3 transverse septa, and a longitudinal septum constricted at the transverse septa (FIG. 8). The causal agent was identified as *Pithomyces chartarum* (Berk. & Curt.) M. B. Ellis. Morphological features were as described for *P. chartarum* (Ahonsi et al. 2010, Ellis 1971).

In the pathogenicity assay, leaf spot symptoms similar to the original disease appeared on plants in each of the eight replicate pots 6 to 10 days post-inoculation. Control plants showed no symptoms. The pathogen was re-isolated from diseased tissues and identified again as *P. chartarum*.

Sequences of the 535 bp PCR amplicons obtained from both isolates were identical. The DNA sequence had 99-100% homology to the ITS sequence of many isolates of *Leptosphaerulina chartarum* (anamorph: *Pithomyces chartarum*), including isolate Mxg-KY09-s4 (GenBank Accession No. GU195649), which had been isolated from leaf spot on *Miscanthus×giganteus* in Kentucky (Ahonsi et al. 2010). To our knowledge, leaf spot caused by *P. chartarum* has not been described on switchgrass as a host (Farr and Rossman 2011). *Pithomyces chartarum* can be seedborne and soil-borne, and has been reported causing leaf spot of smooth bromegrass (*Bromus inermis*) in Nebraska (Eken et al. 2006).

*Sclerotinia homoeocarpa* F. T. Bennett

Figure 9:
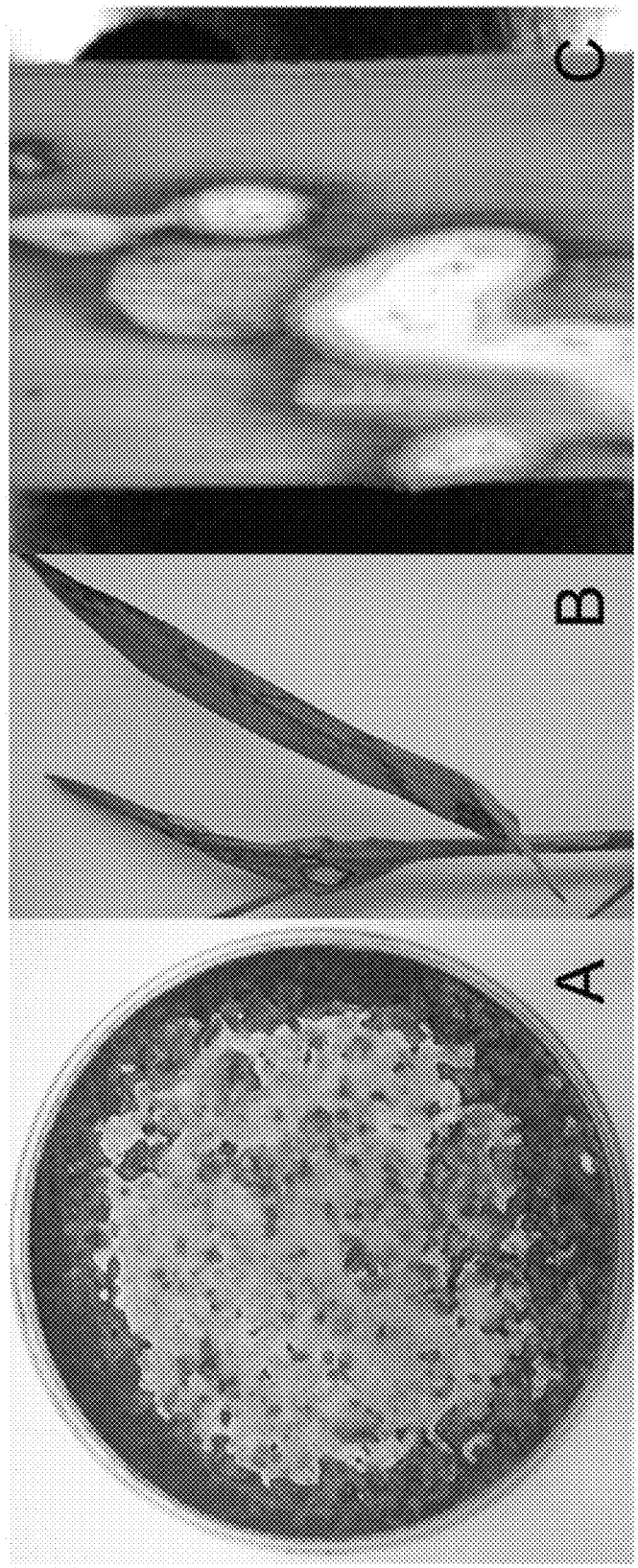
FIGS. 9A-9C.

White, fluffy, aerial mycelium developed within 12 hours of plating on PDA. Viewed from above, colonies were tan to cinnamon in color with a dark brown to black substratal stroma on and in the agar, which appeared brown viewed from below (FIG. 9A). No spores were observed. Morphological characteristics of colony and hyphal growth were identical to those of *Sclerotinia homoeocarpa* F. T. Bennett (Bennett 1937).

Leaf spots appeared as early as 2 days post-inoculation in the pathogenicity assay, with full symptoms after 2 weeks for eight of nine replicates (FIG. 9B, FIG. 9C). Control plants had no symptoms.

PCR amplicons of the ITS region were ~565 bp; sequences of amplicons from the original isolate and re-isolate were identical and submitted to GenBank (Accession No. HQ850151). The ITS sequence had 99% homology with several *Sclerotinia homoeocarpa* isolates in GenBank, including three isolates from buffalo grass in Oklahoma (Accession Nos. EU123800, EU123802, EU123803). The resultant 536-bp fragment was sequenced and submitted to GenBank (accession no. HQ850152); however, there were no SSU sequences from *S. homoeocarpa* available in the database for comparison. To our knowledge, this is the first confirmed report of switchgrass as a natural host for *S. homoeocarpa*, extending the known host range for the pathogen.

Results from this study indicate that diseases caused by well-known fungal pathogens are present on switchgrass in Tennessee. These pathogens are known to cause disease in various grasses and grain crops, including various turf-grasses, miscanthus, wheat, corn, and rice. Management practices for switchgrass may need to be altered to prevent potential disease outbreaks and optimize crop yields. Several pathogens appear to have seedborne transmission. As switch-grass is increasingly grown and cultivated as a biofuels crop, efficient disease management practices and rapid disease identification procedures will likely be necessary.

Switchgrass (*Panicum virgatum* L.) production is increasing in acreage due to current initiatives for commercial biofuel production in the United States and worldwide. Due to a lack of seed certification programs for switchgrass, seed-borne plant pathogens have likely been shipped along with the seeds to switchgrass producers. Management of seed-borne pathogens likely would increase stand establishment and crop yields, while decreasing the likelihood of a seed-borne epidemic.

The aim of this study was to determine if seedborne fungal pathogens were present in switchgrass seed from commercial seed producers in the U.S., and if present, their identity and frequency. Seed of seven cultivars from 11 sources were tested, including multiple entries of 'Alamo', 'Blackwell', 'Cave-in-Rock', and 'Kanlow'. A randomly-selected sub-sample of seed from each 454-g seed lot was surface-sterilized in 1% NaOCl for 1 min, rinsed three times with sterile water, and dried on sterile filter paper. Three hundred surface-sterilized seed per lot were plated on potato dextrose agar (PDA) amended with 100 mg/liter chloramphenicol and incubated at 22° C. Seed were evaluated daily for development of fungal colonies. Emergent colonies were transferred to fresh PDA plates for identification. Rates of fungal infection among the 30 sampled seed lots ranged from less than 1% to 87%. The most frequently evaluated pathogens were *Bipolaris oryzae, Alternaria alternate,* and *Fusarium graminearum/pseudograminearum*. Additional species of *Bipolaris* and *Fusarium* were present, but in lower frequency.

Thirty switchgrass seed lots, including cultivars 'Alamo', 'Blackwell', 'Cave-in-Rock', 'Forestburg', 'Kanlow', 'Cultivar X', and 'Cultivar Y', were obtained from eleven companies in the U.S. (Table 1). Since 'Cultivar X' and 'Cultivar Y' are only available from one company each, the names have been change to prevent interference with the ability of the companies to sell their products. Company names were changed for the same reason.

TABLE 1

Cultivars and source of switchgrass seed

| Cultivar | Company | Company Location | Seed Source |
|---|---|---|---|
| 'Alamo' | Company 1 | CO | TX |
| | Company 2 | NM | TX |
| | Company 3 | PA | MO |
| | Company 5 | OK | OK |
| | Company 6 | OK | OK |
| | Company 7 | KY | TN |
| | Company 8 | KS/CO | OK |
| | Company 9 | TX | TX |
| | Company 10 | OK | OK |
| 'Blackwell' | Company 1 | CO | OK |
| | Company 2 | NM | SD |
| | Company 3 | PA | PA |
| | Company 5 | OK | SD |
| | Company 7 | KY | TN |
| | Company 8 | KS/CO | KS |
| | Company 9 | TX | TX |
| | Company 10 | OK | TX |
| 'Cave-in-Rock' | Company 1 | CO | IL |
| | Company 3 | PA | PA |
| | Company 7 | KY | KY |

TABLE 1-continued

Cultivars and source of switchgrass seed

| Cultivar | Company | Company Location | Seed Source |
|---|---|---|---|
| | Company 8 | KS/CO | KS |
| | Company 11 | IA | IA |
| 'Kanlow' | Company 1 | CO | OK |
| | Company 3 | PA | IA |
| | Company 5 | OK | OK |
| | Company 7 | KY | MO |
| | Company 8 | KS/CO | MO |
| 'Forestburg' | Company 4 | WI | CO |
| 'Cultivar X' | Company 5 | OK | OK |
| 'Cultivar Y' | Company 6 | OK | OK |

A randomly selected subset of seeds from each lot was surface-disinfested with 1% NaOCl (Clorox, Oakland, Calif.) amended with 10 µA Tween 20 (U.S. Biochemical Corp., Cleveland, Ohio) for 1 min with agitation, rinsed three times with sterile deionized water, and dried on sterile filter paper (Mathur and Kongsdal 2003). Three hundred seeds per lot, at a rate of 25 seeds per 9-cm diameter Petri dish, were plated on potato dextrose agar (PDA) amended with 100 mg chloramphenicol/liter of PDA (Sigma-Aldrich, St. Louis, Mo.). Seeds were checked daily for fungal growth. Emergent colonies were transferred to individual PDA plates for identification. Colonies were identified by colony morphology, spore characteristics, and internal transcribed spacer (ITS) region of 18S ribosomal DNA sequences.

Simpson's index of diversity was calculated for each seed lot (Peet 1974). Simpson's index of diversity is the percent likelihood that two organisms randomly picked from the total population are of different species, thus taking into account species richness and abundance.

Nine thousand switchgrass seed were examined for fungal colonization and 2,280 isolates were recovered from these surface-sterilized seed. Of the fungal species recovered, many have been reported as pathogens of switchgrass seedlings or mature plants, including *Alternaria alternata, Bipolaris oryzae, B. sorokiniana, B. spicifera, Curvularia* spp., *Fusarium equiseti, F. graminearum/pseudograminearum* and *F. oxysporum* (Fan and Rossman 2011). In this study, *A. alternata, B. oryzae,* and *F. graminearum/pseudograminearum* were the most commonly isolated pathogenic fungi, with infection rates as high as 38.3, 34.7, and 20.7%, respectively, in some seed lots (Table 2). Several other pathogenic Bipo/aris species, including *B. sorokiniana, B. spicifera,* and *B. victoriae,* and *Fusarium* species, such as *F. equiseti,* were found with less frequency. Overall seedlot infection rates ranged from 0.7-86.8% (Table 3), taking into account that both pathogenic and non-pathogenic fungi were present in some instances.

TABLE 2

Percent infection of switchgrass seed by cultivar, source and fungal species

| | | Fungal species | | | | |
|---|---|---|---|---|---|---|
| Cultivar | Source | *Alternaria alternata* | *Aspergillus* spp. | *Bipolaris oryzae* | *Bipolaris sorokiniana* | *Bipolaris spicifera* |
| 'Alamo' | | | | | | |
| | Company 1 | 3.0 | 0.0 | 0.3 | 0.0 | 0.0 |
| | Company 2 | 4.0 | 0.0 | 1.0 | 0.0 | 0.0 |
| | Company 3 | 6.0 | 0.0 | 1.0 | 0.0 | 0.0 |
| | Company 5 | 0.7 | 0.0 | 0.5 | 0.7 | 0.0 |
| | Company 6 | 13.0 | 0.0 | 0.0 | 0.0 | 0.3 |
| | Company 7 | 2.7 | 0.0 | 0.3 | 0.0 | 0.0 |
| | Company 8 | 1.3 | 13.0 | 0.0 | 0.0 | 0.0 |
| | Company 9 | 0.0 | 0.0 | 0.0 | 0.0 | 0.0 |
| | Company 10 | 0.0 | 0.0 | 0.0 | 0.0 | 0.0 |

TABLE 2-continued

Percent infection of switchgrass seed by cultivar, source and fungal species

'Blackwell'

| | | | | | | |
|---|---|---|---|---|---|---|
| | Company 1 | 5.7 | 0.0 | 0.0 | 0.3 | 0.0 |
| | Company 2 | 1.7 | 0.0 | 0.3 | 0.0 | 0.0 |
| | Company 3 | 0.0 | 0.0 | 0.0 | 0.0 | 0.0 |
| | Company 5 | 0.0 | 0.0 | 0.0 | 0.0 | 0.0 |
| | Company 7 | 3.7 | 0.0 | 0.7 | 0.0 | 0.0 |
| | Company 8 | 29.3 | 0.0 | 0.0 | 0.3 | 0.0 |
| | Company 9 | 38.3 | 0.0 | 0.0 | 0.0 | 0.0 |
| | Company 10 | 0.0 | 0.0 | 14.7 | 0.0 | 0.0 |

'Cave-in-Rock'

| | | | | | | |
|---|---|---|---|---|---|---|
| | Company 1 | 20.3 | 0.0 | 29.7 | 1.7 | 0.0 |
| | Company 3 | 9.5 | 0.0 | 3.5 | 0.0 | 0.0 |
| | Company 7 | 8.7 | 0.0 | 0.7 | 0.0 | 0.0 |
| | Company 8 | 38.3 | 0.0 | 0.0 | 0.0 | 0.0 |
| | Company 11 | 11.3 | 0.0 | 34.7 | 0.3 | 0.0 |

'Kanlow'

| | | | | | | |
|---|---|---|---|---|---|---|
| | Company 1 | 13.3 | 0.0 | 7.7 | 0.0 | 0.0 |
| | Company 3 | 0.0 | 0.0 | 0.0 | 0.0 | 0.0 |
| | Company 5 | 0.0 | 0.0 | 0.0 | 0.0 | 0.0 |
| | Company 7 | 5.7 | 0.0 | 2.0 | 0.0 | 0.0 |
| | Company 8 | 22.5 | 0.0 | 20.0 | 0.3 | 0.0 |

'Forestburg'

| | | | | | | |
|---|---|---|---|---|---|---|
| | Company 4 | 0.0 | 0.0 | 0.0 | 0.0 | 0.0 |

'Cultivar X'

| | | | | | | |
|---|---|---|---|---|---|---|
| | Company 5 | 31.8 | 0.0 | 0.0 | 0.0 | 0.0 |

'Cultivar Y'

| | | | | | | |
|---|---|---|---|---|---|---|
| | Company 6 | 0.7 | 0.0 | 0.0 | 0.0 | 0.0 |

| | | Fungal species | | | | |
|---|---|---|---|---|---|---|
| Cultivar | Source | *Bipolaris victoriae* | *Bipolaris zeicola* | *Chaetomium globosum* | *Curvularia* spp. | *Eurotium* sp. |

'Alamo'

| | | | | | | |
|---|---|---|---|---|---|---|
| | Company 1 | 0.0 | 0.0 | 0.0 | 0.0 | 0.7 |
| | Company 2 | 0.0 | 0.0 | 0.0 | 0.0 | 0.0 |
| | Company 3 | 0.0 | 0.0 | 0.0 | 0.0 | 0.0 |
| | Company 5 | 0.0 | 0.3 | 10.3 | 0.0 | 1.5 |
| | Company 6 | 0.0 | 0.0 | 0.0 | 0.0 | 0.0 |
| | Company 7 | 0.0 | 0.0 | 0.0 | 0.0 | 0.0 |
| | Company 8 | 0.0 | 0.0 | 0.0 | 0.0 | 0.0 |
| | Company 9 | 0.0 | 0.0 | 3.7 | 0.0 | 1.3 |
| | Company 10 | 0.0 | 0.0 | 0.7 | 0.0 | 0.0 |

'Blackwell'

| | | | | | | |
|---|---|---|---|---|---|---|
| | Company 1 | 0.0 | 0.0 | 0.0 | 0.0 | 0.0 |
| | Company 2 | 0.0 | 0.0 | 1.3 | 0.0 | 0.0 |
| | Company 3 | 0.0 | 0.0 | 0.0 | 0.0 | 1.3 |
| | Company 5 | 0.0 | 0.0 | 0.3 | 0.0 | 0.0 |
| | Company 7 | 0.0 | 0.0 | 0.0 | 0.0 | 0.0 |
| | Company 8 | 0.0 | 0.0 | 0.0 | 0.0 | 0.0 |
| | Company 9 | 0.0 | 0.0 | 0.0 | 0.0 | 0.0 |
| | Company 10 | 0.0 | 0.0 | 0.0 | 0.0 | 0.0 |

'Cave-in-Rock'

| | | | | | | |
|---|---|---|---|---|---|---|
| | Company 1 | 0.2 | 0.0 | 0.0 | 0.0 | 0.0 |
| | Company 3 | 0.0 | 0.0 | 0.0 | 0.0 | 0.0 |
| | Company 7 | 0.0 | 0.0 | 0.3 | 0.0 | 0.0 |
| | Company 8 | 0.0 | 0.0 | 0.0 | 0.0 | 0.0 |
| | Company 11 | 0.3 | 0.0 | 0.0 | 0.0 | 0.0 |

'Kanlow'

| | | | | | | |
|---|---|---|---|---|---|---|
| | Company 1 | 0.3 | 0.0 | 0.0 | 0.3 | 0.0 |
| | Company 3 | 0.0 | 0.0 | 0.0 | 0.0 | 0.0 |
| | Company 5 | 0.0 | 0.0 | 3.8 | 0.0 | 8.8 |
| | Company 7 | 0.0 | 0.0 | 3.7 | 0.0 | 3.3 |
| | Company 8 | 0.3 | 0.0 | 0.0 | 0.3 | 0.0 |

TABLE 2-continued

Percent infection of switchgrass seed by cultivar, source and fungal species

'Forestburg'

| | Company 4 | 0.0 | 0.0 | 4.0 | 0.3 | 0.0 |
|---|---|---|---|---|---|---|

'Cultivar X'

| | Company 5 | 0.0 | 0.0 | 1.0 | 0.3 | 0.0 |
|---|---|---|---|---|---|---|

'Cultivar Y'

| | Company 6 | 0.0 | 0.0 | 0.0 | 0.0 | 0.0 |
|---|---|---|---|---|---|---|

| | | Fungal species | | | | |
|---|---|---|---|---|---|---|
| Cultivar | Source | *Fusarium equiseti* | *Fusarium graminearum/ pseudo-graminearum* | *Fusarium oxysporum* | *Fusarium* spp. | *Penicillium* spp. |
| 'Alamo' | | | | | | |
| | Company 1 | 0.0 | 0.0 | 0.0 | 0.0 | 0.0 |
| | Company 2 | 0.0 | 0.3 | 0.0 | 0.7 | 0.0 |
| | Company 3 | 2.7 | 7.7 | 0.0 | 7.3 | 0.3 |
| | Company 5 | 0.0 | 0.0 | 0.0 | 0.0 | 0.0 |
| | Company 6 | 0.0 | 0.0 | 0.0 | 0.0 | 0.0 |
| | Company 7 | 0.0 | 0.2 | 4.5 | 31.3 | 0.7 |
| | Company 8 | 0.0 | 0.0 | 0.0 | 0.0 | 3.0 |
| | Company 9 | 0.0 | 0.7 | 0.0 | 0.0 | 0.0 |
| | Company 10 | 0.0 | 0.0 | 0.0 | 0.0 | 0.0 |
| 'Blackwell' | | | | | | |
| | Company 1 | 2.7 | 0.0 | 0.0 | 0.7 | 0.0 |
| | Company 2 | 0.0 | 0.7 | 0.0 | 1.3 | 0.3 |
| | Company 3 | 0.0 | 0.0 | 0.0 | 1.0 | 2.7 |
| | Company 5 | 0.0 | 0.0 | 0.0 | 0.0 | 0.7 |
| | Company 7 | 0.0 | 1.2 | 0.0 | 4.0 | 0.3 |
| | Company 8 | 0.0 | 0.0 | 0.0 | 0.0 | 0.0 |
| | Company 9 | 0.0 | 1.5 | 0.0 | 0.0 | 0.0 |
| | Company 10 | 0.0 | 0.0 | 0.0 | 0.0 | 0.0 |
| 'Cave-in-Rock' | | | | | | |
| | Company 1 | 0.0 | 0.0 | 5.0 | 1.0 | 0.0 |
| | Company 3 | 0.0 | 20.7 | 0.0 | 12.8 | 0.0 |
| | Company 7 | 0.0 | 0.0 | 0.0 | 1.0 | 0.7 |
| | Company 8 | 0.0 | 0.0 | 0.0 | 0.7 | 0.0 |
| | Company 11 | 0.0 | 0.0 | 0.0 | 0.0 | 0.3 |
| 'Kanlow' | | | | | | |
| | Company 1 | 0.0 | 0.0 | 0.0 | 10.7 | 0.0 |
| | Company 3 | 0.0 | 0.0 | 0.0 | 0.0 | 0.0 |
| | Company 5 | 0.0 | 0.0 | 0.0 | 0.0 | 0.0 |
| | Company 7 | 0.0 | 0.3 | 0.0 | 7.0 | 0.0 |
| | Company 8 | 0.0 | 4.0 | 0.0 | 12.7 | 2.5 |
| 'Forestburg' | | | | | | |
| | Company 4 | 0.0 | 0.0 | 0.0 | 1.7 | 0.0 |
| 'Cultivar X' | | | | | | |
| | Company 5 | 0.0 | 4.7 | 0.0 | 8.5 | 0.0 |
| 'Cultivar Y' | | | | | | |
| | Company 6 | 0.0 | 0.0 | 0.0 | 0.0 | 0.0 |

| | | Fungal species | | | | | |
|---|---|---|---|---|---|---|---|
| Cultivar | Source | *Phoma* sp. | *Pithomyces chartarum* | *Xylaria* sp. | Zygo-mycetes | Unidentified brown Ascomycete | Un-Identified fungi |
| 'Alamo' | | | | | | | |
| | Company 1 | 0.0 | 0.0 | 0.3 | 0.0 | 0.0 | 0.0 |
| | Company 2 | 1.7 | 0.0 | 0.0 | 0.0 | 0.0 | 1.0 |
| | Company 3 | 2.0 | 0.0 | 0.0 | 0.0 | 0.0 | 2.3 |
| | Company 5 | 0.0 | 0.0 | 0.0 | 0.0 | 0.0 | 0.0 |
| | Company 6 | 2.0 | 0.0 | 0.7 | 0.0 | 0.0 | 0.7 |
| | Company 7 | 0.0 | 0.0 | 0.0 | 0.0 | 0.0 | 0.0 |
| | Company 8 | 0.7 | 0.0 | 0.3 | 7.7 | 0.0 | 0.7 |

TABLE 2-continued

Percent infection of switchgrass seed by cultivar, source and fungal species

|  |  |  |  |  |  |  |  |
|---|---|---|---|---|---|---|---|
|  | Company 9 | 0.0 | 0.0 | 0.0 | 0.0 | 0.0 | 0.0 |
|  | Company 10 | 0.3 | 0.0 | 0.0 | 0.0 | 0.0 | 1.7 |
| 'Blackwell' |  |  |  |  |  |  |  |
|  | Company 1 | 0.0 | 0.0 | 0.0 | 0.0 | 0.0 | 2.3 |
|  | Company 2 | 0.3 | 0.0 | 0.7 |  | 6.3 | 0.0 |
|  | Company 3 | 2.0 | 0.0 | 0.0 | 0.0 | 0.0 | 2.0 |
|  | Company 5 | 0.0 | 0.0 | 0.0 | 0.0 | 0.0 | 0.3 |
|  | Company 7 | 12.8 | 0.0 | 0.0 | 0.0 | 0.0 | 1.0 |
|  | Company 8 | 0.0 | 0.0 | 0.3 | 0.0 | 0.0 | 1.0 |
|  | Company 9 | 0.3 | 0.0 | 4.2 | 0.0 | 0.0 | 0.0 |
|  | Company 10 | 1.0 | 0.0 | 0.0 | 0.0 | 0.0 | 0.3 |
| 'Cave-in-Rock' |  |  |  |  |  |  |  |
|  | Company 1 | 25.5 | 0.0 | 1.2 | 0.0 | 0.0 | 2.3 |
|  | Company 3 | 0.0 | 0.3 | 0.2 | 0.0 | 0.0 | 5.7 |
|  | Company 7 | 0.3 | 0.0 | 0.0 | 2.0 | 0.0 | 1.7 |
|  | Company 8 | 0.3 | 0.0 | 0.3 | 0.0 | 0.0 | 0.0 |
|  | Company 11 | 4.7 | 0.0 | 0.0 | 0.0 | 0.0 | 0.0 |
| 'Kanlow' |  |  |  |  |  |  |  |
|  | Company 1 | 0.0 | 0.0 | 0.0 | 0.0 | 0.0 | 0.0 |
|  | Company 3 | 0.0 | 0.0 | 0.0 | 0.0 | 0.0 | 0.7 |
|  | Company 5 | 0.0 | 0.0 | 0.0 | 0.0 | 0.0 | 0.0 |
|  | Company 7 | 3.7 | 0.0 | 0.0 | 0.0 | 0.0 | 0.0 |
|  | Company 8 | 7.0 | 2.5 | 0.3 | 0.0 | 0.0 | 6.7 |
| 'Forestburg' |  |  |  |  |  |  |  |
|  | Company 4 | 0.0 | 0.0 | 0.0 | 6.0 | 0.3 | 0.0 |
| 'Cultivar X' |  |  |  |  |  |  |  |
|  | Company 5 | 3.7 | 0.0 | 0.3 | 0.0 | 0.0 | 0.3 |
| 'Cultivar Y' |  |  |  |  |  |  |  |
|  | Company 6 | 0.0 | 0.0 | 0.0 | 0.0 | 0.0 | 0.7 |

TABLE 3

Total percent switchgrass seed infection and diversity analysis by cultivar and source

| Cultivar | Source | Total percent infection | Total percent *Bipolaris* spp. infection | Total percent *Fusarium* spp. infection | Simpson's Index of Diversity[1] |
|---|---|---|---|---|---|
| 'Alamo' |  |  |  |  |  |
|  | Company 1 | 4.3 | 0.3 | 0.0 | 52.56 |
|  | Company 2 | 8.7 | 1.0 | 1.0 | 77.78 |
|  | Company 3 | 29.3 | 1.0 | 17.7 | 81.61 |
|  | Company 5 | 14.0 | 1.5 | 0.0 | 44.8 |
|  | Company 6 | 16.7 | 0.3 | 0.0 | 38.12 |
|  | Company 7 | 39.7 | 0.3 | 36.0 | 36.13 |
|  | Company 8 | 26.7 | 0.0 | 0.0 | 67.15 |
|  | Company 9 | 5.7 | 0.0 | 0.7 | 54.41 |
|  | Company 10 | 2.7 | 0.0 | 0.0 | 60.71 |
| 'Blackwell' |  |  |  |  |  |
|  | Company 1 | 11.7 | 0.3 | 3.3 | 68.74 |
|  | Company 2 | 13.0 | 0.3 | 2.0 | 73.68 |
|  | Company 3 | 9.0 | 0.0 | 1.0 | 80.91 |
|  | Company 5 | 1.3 | 0.0 | 0.0 | 66.67 |
|  | Company 7 | 23.7 | 0.7 | 5.2 | 65.74 |
|  | Company 8 | 31.0 | 0.3 | 0.0 | 8.48 |
|  | Company 9 | 44.3 | 0.0 | 1.5 | 24.42 |
|  | Company 10 | 16.0 | 14.7 | 0.0 | 15.87 |
| 'Cave-in-Rock' |  |  |  |  |  |
|  | Company 1 | 86.8 | 31.5 | 6.0 | 74.03 |
|  | Company 3 | 52.7 | 3.5 | 33.5 | 74.28 |
|  | Company 7 | 15.3 | 0.7 | 1.0 | 64.14 |
|  | Company 8 | 39.7 | 0.0 | 0.7 | 6.62 |
|  | Company 11 | 51.7 | 35.3 | 0.0 | 49.66 |

TABLE 3-continued

Total percent switchgrass seed infection and
diversity analysis by cultivar and source

| Cultivar | Source | Total percent infection | Total percent *Bipolaris* spp. infection | Total percent *Fusarium* spp. infection | Simpson's Index of Diversity[1] |
|---|---|---|---|---|---|
| 'Kanlow' | | | | | |
| | Company 1 | 32.3 | 8.0 | 10.7 | 67.16 |
| | Company 3 | 0.7 | 0.0 | 0.0 | 0 |
| | Company 5 | 12.7 | 0.0 | 0.0 | 43.35 |
| | Company 7 | 25.7 | 2.0 | 7.3 | 82.37 |
| | Company 8 | 79.2 | 20.7 | 16.7 | 81.37 |
| 'Forestburg' | | | | | |
| | Company 4 | 12.3 | 0.0 | 1.7 | 65.62 |
| 'Cultivar X' | | | | | |
| | Company 5 | 50.7 | 0.0 | 13.2 | 56.66 |
| 'Cultivar Y' | | | | | |
| | Company 6 | 1.3 | 0.0 | 0.0 | 66.67 |

[1]Simpson's Index of Diversity = $1 - (\Sigma^s_{i=1} P_i^2)$, where $P_i$ = proportion of all individuals belonging to the $i^{th}$ species In this study, several fungal pathogens of switchgrass that were not previously shown to have seedborne transmission were isolated directly from seed. 'Cave-in-Rock' appears to be more susceptible to seedborne infection with the known pathogens, but statistical analysis was not performed. Although no direct correlation between cultivar, company, or seed source location and percent infection by the known pathogens was determined, the information provided by this study may help to prevent the seedborne movement of pathogens around the country and around the world, and explain the movement of switchgrass pathogens, such as *B. oryzae*. *Bolaris oryzae*, which was found in 50% of the seed lots tested, including cultivars 'Alamo', 'Blackwell', 'Cave-in-Rock', and 'Kanlow' (Table 2), has been reported from many locations around the United States, including New York, North Dakota, Mississippi, and Oklahoma. Some of these reports have been descriptions of severe outbreaks (Waxman and Bergstrom 2011, Krupinsky et al. 2004, Tomaso-Peterson et al. 2010, and Ghimire et al. 2011). Further studies will be needed to determine/confirm species identity and pathogenicity of several fungi isolated from seed, including *Phoma* sp., *Curvularia* spp., *Fusarium* spp., *Bipolaris victoriae*, and *Bolaris zeicola*.

The most frequently isolated species were *Alternaria alternata*. This pathogen has a broad host range, including over 900 host species (Farr and Rossman 2011). *Alternaria alternata* can cause disease on wheat and rice, in addition to inducing problems in humans as an environmental allergen causing chronic sinusitis and as a cause of esophageal cancer when the mycotoxins produced on grains (including wheat) are ingested (Liu et al. 1991, Liu et al. 1992). This fungus can survive for a long time as a saprophyte in soil, and mycotoxin production may prove problematic for bioethanol conversion from switchgrass infected with *A. alternata*.

Another large group of fungi identified are the anamorphic stages of *Cochliobolus: Bolaris* and *Curvularia*. Both genera contain pathogens of a range of grass hosts, including turfgrasses, sorghum, wheat, corn, and oat. These pathogens frequently can survive in soil, which may need to be taken into account for crop rotations, particularly in the southeastern U.S.

Several species of *Fusarium* were isolated from seed in this study, and more work needs to be done to confirm species identity. Several of the species also were identified from mature plants grown in fields or in ornamental plots in Tennessee in previous work, including *Fusarium graminearum/pseudograminearum* and *Fusarium equiseti* (See Chapter 2 of this thesis). Both *F. graminearum/pseudograminearum* and *F. equiseti* are likely to cause disease problems in switchgrass necessitating the development of management practices. Species of *Fusarium* can also produce mycotoxins that could interfere with the biomass conversion process, which uses microbial and enzymatic digestion and fermentation of sugars to produce ethanol. Further studies will need to be conducted to assess the effect of mycotoxin presence on overall bioethanol yield.

Another well-known mycotoxin producer found in this study was *Pithomyces chartarum*, which can also causes diseases of sheep and other livestock. *Pithomyces chartarum* was not found frequently in this study, but had previously been isolated from switchgrass grown in a growth chamber for pot studies. *Phoma* sp. also was reported previously on switchgrass, but pathogenicity was not determined (Farr and Rossman 2011). *Phoma* can cause diseases on related grasses, such as wild rice (Nyvall and Percich 1999).

Species of *Xylaria*, *Eurotium*, and *Chaetomium* are likely to be non-pathogenic endophytes. More studies will be needed to determine if any of these fungi have an effect on growth of switchgrass. When measures are taken to decrease overall fungal infection of seed, presence or absence of species of these genera may not have any effect on overall switchgrass growth or stand establishment.

More work will need to be conducted to determine the best management plan for these pathogens. Likely, decreasing inoculum levels in the field will have a profound effect on overall seed infection rates. Seed treatments may be explored as an effective control method if germination and emergence problems become limiting factors in establishing a quality stand.

Switchgrass-derived ethanol is currently being investigated as a renewable energy source alternative to fossil fuel. However, conversion of switchgrass biomass to ethanol is still being optimized. Previous studies have shown that switchgrass-derived extractives can contain phenolic compounds associated with antimicrobial activity. Due to the microbial and enzymatic involvement in many systems for saccharification and fermentation of plant material in the conversion to ethanol, antimicrobial activity could decrease overall ethanol yield. In this study, switchgrass extractives were evaluated for antimicrobial activity. Six ethanol-soluble extractives treatments, extracted from switchgrass collected from three farms at two different plant ages, were tested in a 3×2 factorial design against four bacterial plant pathogens: *Clavibacter michiganensis* subsp. *michiganensis, Xanthomonas perforans, Pseudomonas syringae* pv. *tomato*, and *Pseudomonas mediterranea*. Significant differences were shown for the main effect of bacteria (P=0.09) and the interaction effect of farm×plant age (P=0.04). *Xanthomonas perforans* was more sensitive to the extractives treatments than *Pseudomonas syringae* pv. *tomato* and extractives from 112 day-old switchgrass from farm C04 inhibited bacterial growth more than the extractives from 112 day-old switchgrass from farms C19 and C33. There was no difference in bacterial inhibition among farms for the extractives from 56 day-old switchgrass plants. In addition to increasing the overall ethanol yield per gram of plant tissue, removal of the extractives and use of these compounds as an antimicrobial agent will lead to the use of the extractives as a value-added product to the biomass conversion system.

Four plant pathogenic bacteria were tested for susceptibility to antimicrobial activity by switchgrass-derived extractives: *Clavibacter michiganensis* subsp. *michiganensis, Xanthomonas perforans, Pseudomonas syringae* pv. *tomato*, and *Pseudomonas mediterranea*. All species were from culture collections maintained by Dr. Bonnie Ownley (University of Tennessee) and are known to be pathogenic on tomato. *Clavibacter michiganensis* subsp. *michiganensis* (CMM), *Xanthomonas perforans* (XS), and *Pseudomonas syringae* pv. *tomato* (PST) were isolated from tomato and *Pseudomonas mediterranea* (PM) was isolated from soybean. Each culture was shaken overnight in tryptic soy broth. Cultures were centrifuged for 3 min at 4,200×g in an Eppendorf 5810 centrifuge (Eppendorf AG, Hamburg, Germany). Broth was then removed and each culture was resuspended in phosphate buffered saline (PBS) at a concentration of approximately $1 \times 10^8$ CFU/ml.

Controls consisted of 0.5 ml 10% ethanol and 0.5 ml bacterial solution in PBS for each bacterial isolate. These solutions were incubated at 22° C. on the laboratory benchtop for 60 min. Solutions were then diluted with PBS to $10^{-5}$, $10^{-6}$, and $10^{-7}$ of the original dilution and plated on tryptic soy agar in duplicate. Plates were counted and dilution plates with colony counts in the range of 30 to 300 were used for data analysis. The experiment was replicated over time with three trials, and one replicate per trial. The mean of population counts of two dilution plates was used for each replicate.

Extractives

Six groups of 'Alamo' switchgrass were harvested from three different farms in Vonore, Tenn. at two different plant ages (Table 4). The extractives from each sample were separated with 95% ethanol (Decon Laboratory, Inc., PA, USA) using a Dionex Accelerated Solvent Extractor (Dionex, Sunnyvale, Calif.). Ethanol was driven off with an HBA 10 Digital Rotary Evaporator (IKA, Germany) and Model 281A Vacuum Oven (Fisher Scientific, PA, USA). This work was conducted by Dr. Paul Filson and Britany Swann. Samples were stored at 4° C. in darkness until experiments were performed.

For each extractives sample, 125 mg of dry extractives material was dissolved in 4 ml of 10% ethanol solution, vortexed, sonicated for three 1-min intervals, and cold-sterilized with a 0.2-μm filter into a sterile glass vial. Total phenolics were measured following the Folin-Ciocalteau analysis procedure (Waterhouse 2002) and with a UV 160U UV-visible recording spectrophotometer (Shimadzu Corporation, Kyoto, Japan).

TABLE 4

Source and plant age of six 'Alamo' selections from which extractives were obtained

| Farm | Plant age (in days) |
|---|---|
| C04 | 56 |
| C04 | 112 |
| C19 | 56 |
| C19 | 112 |
| C33 | 56 |
| C33 | 112 |

Treatments

Antimicrobial activity of extractives was tested by making a 50% (v/v) solution of 0.5 ml extractives solution and 0.5 ml bacterial solution in PBS for each of the six extractives for each bacterial isolate. Controls consisted of 0.5 ml 10% ethanol and 0.5 ml bacterial solution in PBS for each bacterial isolate. These solutions were incubated at 22° C. on the laboratory benchtop for 60 min. Solutions were then diluted with PBS to $10^{-5}$, $10^{-6}$, and $10^{-7}$ of the original dilution and plated on tryptic soy agar in duplicate. Plates were counted and dilution plates with colony counts in the range of 30 to 300 were used for data analysis. The experiment was replicated over time with three trials, and one replicate per trial. The mean of population counts of two dilution plates was used for each replicate.

Experimental Design and Statistical Analysis

The experimental setup was a 3×2 factorial with three farm locations and two plant ages. The variable Log(Treatment Population Count+1) was calculated for each combination of bacteria and extractives, and bacteria and control.

Population growth was determined as a percentage control:

$$\frac{\text{Log 10(Treatment Population Count} + 1)}{\text{Log 10(Control Population Count} + 1)} \times 100$$

The main effects and interactions of extractives and bacteria on this variable were analyzed for significance with the Proc Mixed procedure of SAS 9.2 software (SAS Institute, Cary, N.C.). Significant effects and interactions were further analyzed with a Fisher's-protected least significant difference (F-LSD) test at P=0.05 and P=0.10.

Results and Discussion

Total Phenols

Total phenolic concentrations varied from 7.19 to 21.06 mg GAE per g dry extractives

TABLE 5

Total phenolic concentrations

| Farm | Plant age (in days) | mg GAE[1]/g extractives |
|---|---|---|
| C04 | 56 | 7.19 ± 0.97 |
| C04 | 112 | 12.17 ± 1.00 |
| C19 | 56 | 13.81 ± 5.49 |
| C19 | 112 | 12.45 ± 0.93 |
| C33 | 56 | 21.06 ± 2.92 |
| C33 | 112 | 8.03 ± 0.87 |

[1]GAE = Gallic acid equivalent. Values are the mean of three replicates ± standard error.

Bacterial Inhibition

Figure 10:
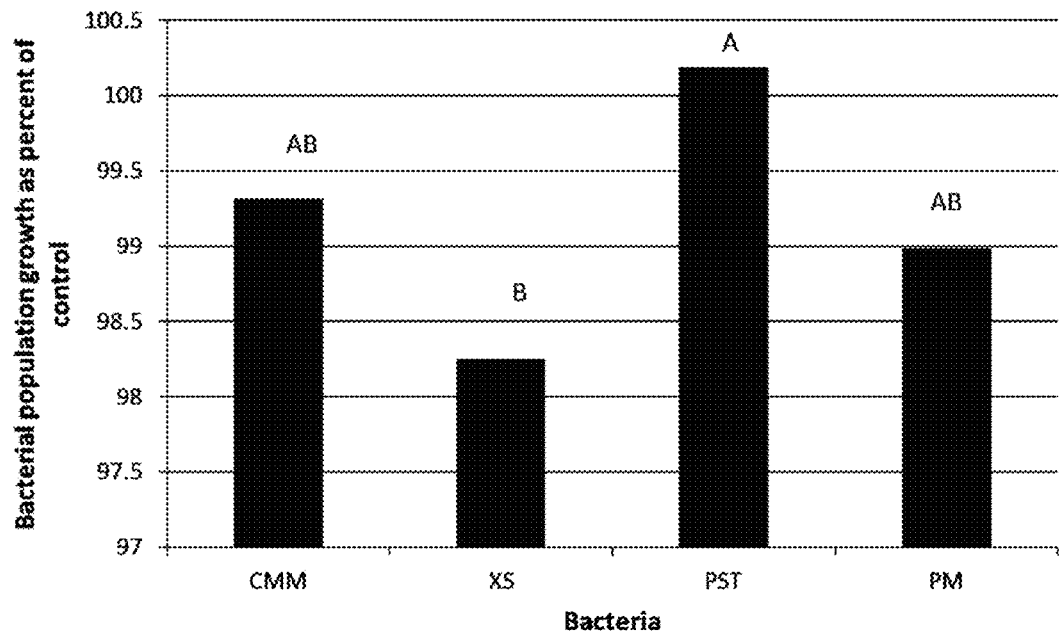
FIG. 10. Effect of bacterial species on percent growth compared to control. CMM=*Clavibacter michiganensis* subsp. *michiganensis*, XS=*Xanthomonas perforans*, PST=*Pseudomonas syringae* pv. *tomato*, PM=*Pseudomonas mediterranea*.
Figure 11:
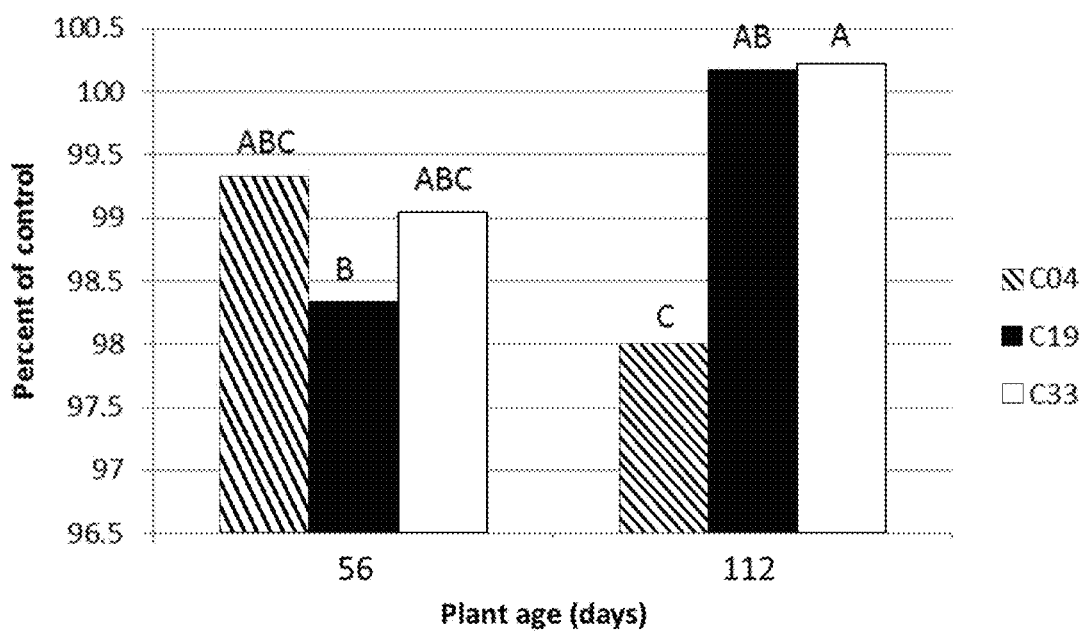
FIG. 11. Effect of the interaction of harvest date×farm on bacterial population growth as a percent of control. CO4, C19, C33 are designations for farms where switchgrass was produced. Bars with the same letters are not significantly different according to an F-protected LSD at P=0.05.

The main effect of bacteria (P=0.0967) and the interaction of farm×plant age (P=0.0494) were significant for population growth as a percentage of control. *Xanthomonas perforans* was significantly more sensitive to the extractives treatments overall than *Pseudomonas syringae* pv. *tomato* (FIG. 10). A significant difference was also shown between farm C04 and farm C19 and C33 for plant age=112 days, in which switchgrass extractives from farm C04 had more antimicrobial activity than extractives from C19 and C33 (FIG. 11).

Analysis of the data indicated that significant effects exist. *Xanthomonas* appears to be more susceptible than the other plant pathogens. As the age of plants at harvest increased, the extractives collected from plants on farm C04 had more activity than plants from other locations collected at the same plant age. Since the same cultivar was used, differences in activity of extractives could be due to differences in abiotic and biotic environmental conditions at these locations. Studies of in vitro activity of similar switchgrass-derived extractives against food-borne *Salmonella* pathogens showed some activity (Doris D'Souza, personal communication). Due to the environmental stability of the plant pathogens tested in this study, a longer incubation time may be needed for exposure of the bacteria to the extractives to have a significant effect on bacterial population growth. It is likely that these plant pathogens have evolved to be more tolerant of plant defense compounds than food-borne animal pathogens such as *Salmonella*. Similar compounds have activity against fungal plant pathogens, such as *Fusarium oxysporum*; (Mandal et al. 2009) so extractives may provide a source of antifungal compounds as well as antibacterial compounds. The variations in total phenolics in this study could be further understood with analysis of the specific compounds that make up the total.

The results of this project provide information that will be integral for the development of disease management practices and seed certification programs for switchgrass in Tennessee. Nine fungal pathogens were identified from mature switchgrass grown in Tennessee, and at least five fungal pathogens were isolated directly from switchgrass seed produced in the United States and shipped to Tennessee. As the biofuels initiative at the University of Tennessee moves forward, disease management practices and seed certification programs could significantly increase both the commercial and overall success of the switchgrass-derived cellulosic ethanol program. Further studies into the effect of fungal infection on extractives composition, fermentable sugar yield per gram biomass, and total cellulosic ethanol yield per gram biomass will need to be conducted to determine the overall effect of fungal infection on the cellulosic ethanol system of switchgrass. The ethanol-soluble extractives of switchgrass show some antibacterial activity, and further studies will be needed to determine optimal extractives concentration and treatment conditions, as well tests for antifungal activity and economic and energy-expenditure studies for the feasibility of removing ethanol-soluble extractives prior to the pretreatment stage of the biomass conversion process of switchgrass.

Switchgrass Extracts Against Animal and Plant Pathogens and its Anti-Inflammatory Properties Nonstructural compounds naturally present in noteworthy amounts in switchgrass, a dedicated bioenergy feedstock for the Southeastern U.S., were found effective 1) to protect plants against pathogen *Xanthomonas perforans,* 2) to inhibit food-borne pathogen *Salmonella typhimurium*, and 3) to reduce production of pro-inflammatory cytokines by fat cells. Here, in certain embodiments we are proposing to isolate and purify this switchgrass fraction by a single solvent extraction to generate a high value-added product that will be utilized for the various applications cited above. Moreover, the removal of certain inhibitory compounds during this extraction step, prior to the pretreatment and conversion of biomass, would positively impact the yield of biofuel produced from the cellulosic fraction.

The optimal extraction and utilization of these non-structural switchgrass compounds would present economical, ecological, agricultural, and health benefits. For example, switchgrass extracts via reduction of obesity-associated inflammation may benefit people with type 2 diabetes as reducing inflammation improves glucose metabolism. Moreover, it is estimated that as high as 50% loss of marketable fruit is due to bacterial spot on tomatoes. As existing chemical controls provide only marginal success, switchgrass extracts could play an important role in controlling bacterial diseases.

When integrated to a biofuel production system, switchgrass extracts can offer enormous opportunities for increasing the sustainability of agriculture by not only improving the production of energy, but by also generating a stream for high-value products with potential benefits for agriculture and human health.

Physico-chemical, structural, and compositional factors affect the performance of biomass in a biorefinery. Efficiency of enzymatic conversion of lignocellulosic substrates to 2 fuels such as ethanol and butanol is influenced by various properties of the substrate at different levels; microfibril, fibril, and fiber. In biochemical conversion, specific constituents of ash or extractives could act as inhibitors during the conversion process (depending on the tolerance and resistance of the organisms involved in the process, along with enzymes that remain active in the presence of these substances). On the other hand, dedicated energy crops such as switchgrass can offer enormous opportunities for increasing the sustainability of agriculture by not only producing energy, but by also generating a stream of high-value products with potential benefits for agriculture and human health.

In a pilot scale biorefinery scenario, 3,000 tons of switchgrass per year are needed to produce 250,000 gallons of ethanol. Of these 3,000 tons, 450 tons will be extractives (based on 15% of extractives). In a commercial scale biorefinery where 20 million gallons are the target, 36,000 tons of extractives will be available, the use of which is yet to be explored.

While the effects of extractives on cellulosic fermentation are not completely known, phenolics, such p-coumaric and ferulic acids, have been implicated as inhibitors of ruminal fermentation of cell wall polysaccharides; in vitro digestibility of grasses was negatively correlated with the ratio of p-coumaric to ferulic acid of the forage (Jung and Shalita-Jones 1990). Extractives are inhibitors in the biochemical conversion of switchgrass into fuels but contain chemicals with high value and novel applications that are beneficial to agriculture and human health. In certain embodiments, we are proposing to extract this fraction prior to the pretreatment and conversion steps in order to generate a new stream that has great potential applications and in the same time by removing free sugars and phenolic components we generate a cleaner cellulosic biomass for biofuel production.

Improving biofuel conversion efficiency of switchgrass, while simultaneously utilizing the extractives naturally present in the plant tissues as high value-added products, would have potential benefits in agriculture and human health. In the long term, we envision to increase the value of the characterized bioactive compounds in switchgrass extractives since many of them have potential applications in human health, and for control of microbial pathogens. For example, antimicrobial compounds (e.g. polyphenolics, aromatics) can be effective in protection of plants against pathogens, prevention of food spoilage, and inhibition of food-borne pathogens, thus enhancing food quality and safety. Antimicrobial compounds such as p-coumaric and ferulic acids, and steroidal saponins are associated with induced resistance to plant pathogens (Panina et al. 2007). The induced resistance response, in which plants react to the presence of a pathogen by a rapid expression of defense-related genes, is systemic and compounds accumulate in leaves even if roots are the site of pathogen attack. The antimicrobial phenolics in switchgrass extractives could in certain embodiments be used for protection of plants and foods against microbial attack/contamination and degradation. Outbreaks of illnesses linked to various foodborne pathogens and emerging pathogens that are becoming resistant to current treatment processes and are increasingly drug resistant (such as multidrug resistant *Salmonella* and methicillin resistant *Staphylococcus aureus*) are gaining much attention. Food safety and food biosecurity are important public global concerns and novel approaches to maintain food safety and security are needed. Novel value-added products that could have potential effects against these pathogens are in growing demand. Similarly, obesity is a growing epidemic problem worldwide and is associated with several metabolic disorders such as diabetes and cardiovascular disease. Inflammation is the basis for most of these disorders and current research has turned to bioactive compounds in plants and food with anti-inflammatory properties to treat or prevent these diseases (Kim and Moustaid 2000). Furthermore, characterization of inhibitory substances that decrease the efficiency of bioconversion can be used to obtain mutant yeasts or recombinant enzymes that are tolerant or resistant to the extractives and will ultimately improve the efficiency of fuels bioconversion, increasing the yield at a faster rate. Moreover, the bioactive components could have the potential for commercialization for use as bioactive ingredients for application in agriculture as well as for human consumption.

In exemplary embodiments, we harvested switchgrass samples (after the first frost) from three UT switchgrass fields (C04, C19 and Windham). The samples were ground under liquid nitrogen and extracted immediately with ethanol. The 3 extracts were then tested against bacterial plant pathogen *Xanthomonas perforans*, foodborne pathogens, and for their anti-inflammatory properties.

Figure 12:
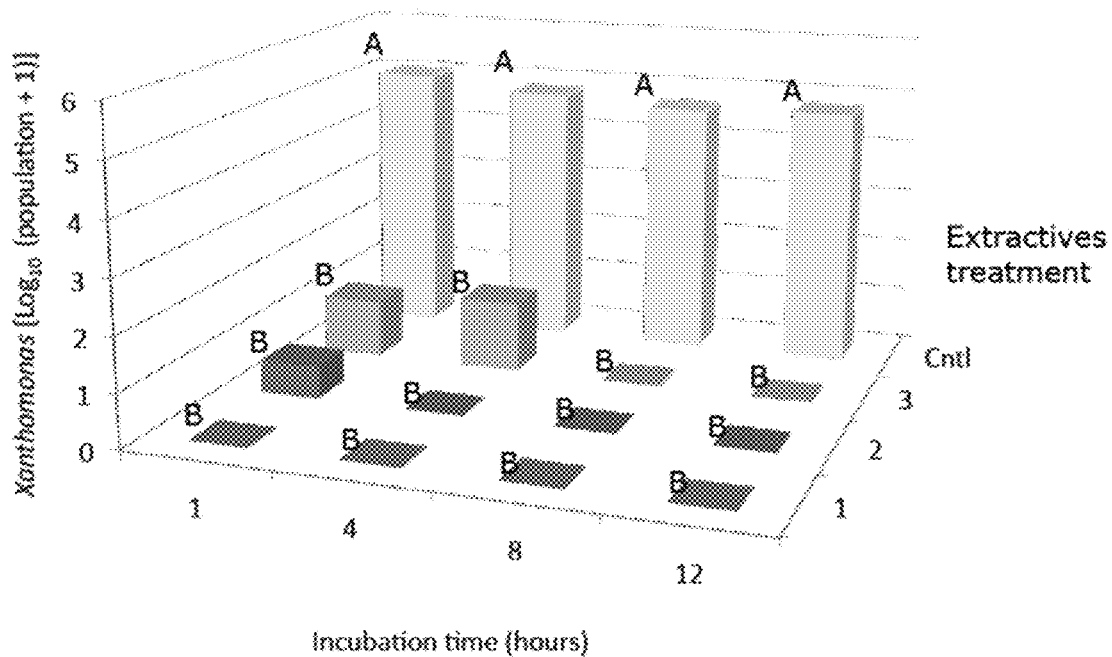
FIG. 12. Effects of three switchgrass extracts on *X. perforans* population after various incubation times.

The crude switchgrass extracts were evaluated for antimicrobial activity by mixing with high populations ($2 \times 10^8$ CFU/ml) of *X. perforans*, and incubating at four time periods. After treating with the switchgrass extracts for 8- and 12-h, *X. perforans* could not be detected in any of the extractives treatments (FIG. 12). Small populations were found in Windham extracts (treatment 3), after 1- and 4-h incubation, and after 1-h incubation for sample C19 (treatment 2). No *X. perforans* colonies were detected after incubation at any of the time points with sample C04 (treatment 1). The control contained *X. perforans* at 5-log after the 1-h incubation, decreasing to 4-log for longer incubation periods. The effects of incubation time (P=0.5364) and the interaction of extractives and incubation time (P=0.9578) were not significant. For the main effect of extractives treatment on *Xanthomonas* population, all extractives treatments were significantly different from the control at all incubation times (P=0.0001).

*Xanthomonas* populations were inhibited by all extracts treatments at 8- and 12-hincubations with extracts C04 (treatment 1) being the most effective as no colonies of *X. perforans* were detected even after only 1-hr incubation.

In the United States alone, *Salmonella* associated outbreaks cost more than $2.5 billion annually, with around 40,000 annual cases. There are more than 2,500 serovars of *Salmonella* that are capable of causing human disease, the predominant ones being *Salmonella Typhimurium* and *S. Enteritidis*. After 6 hour incubation time, *Salmonella Typhimurium* population was found to be impacted by the extracts treatment (Table 6). Further tests with longer incubation times, other extracts and also with *Escherichia coli* O157:H7 are on-going.

TABLE 6

Recovery of 2 types of *Salmonella* after 6 hour switchgrass extracts treatment

| Recovery after 6 hours log CFU/mL | Control (5% ethanol) | Switchgrass extract (CO4) |
|---|---|---|
| *Salmonella Typhimurium* | 7.86 ± 0.36 (A) | 7.07 ± 0.26 (B) |
| *Salmonella Enteritidis* | 6.78 ± 0.61 (A) | 6.61 ± 0.26 (A) |

Different letters indicate significant differences at $p < 0.05$

Figure 13:
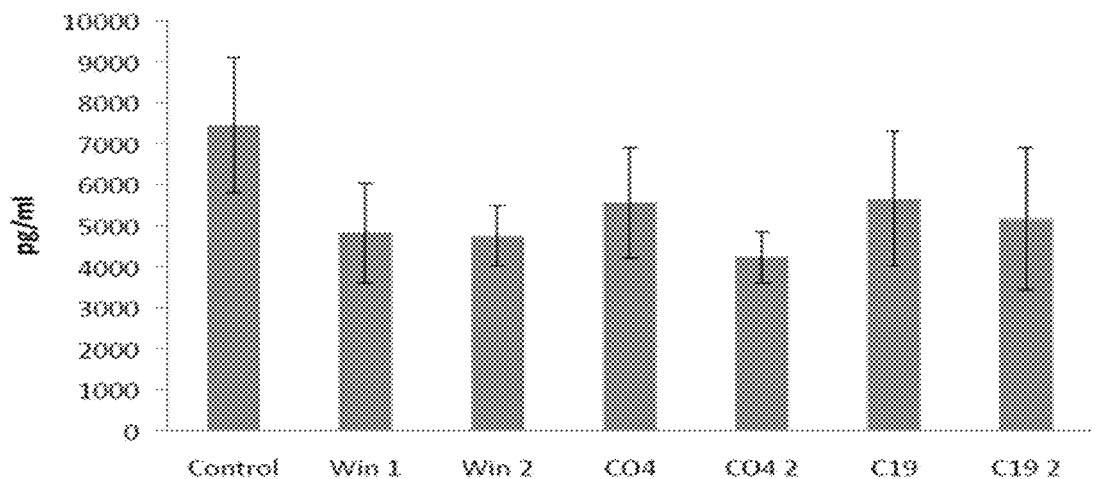
FIG. 13. Effects of switchgrass extracts on monocyte chemotactic protein-1.

The anti-inflammatory properties of the extracts were tested on differentiated 3T3-L1 (Mouse embryonic fibroblast cells). Our data indicate that switchgrass extracts can reduce inflammation and production of inflammatory cytokines from fat cells such as MCPa (FIG. 13).

Inflammation is now recognized as a basis for obesity and associated metabolic disorders such as type 2 diabetes. Thus, the potential impact of this research is that the switchgrass extracts via reduction of inflammation may benefit people who have obesity and diabetes by reducing inflammation and improved glucose metabolism.

REFERENCES

Agindotan, B. O., Ahonsi, M. O., Gray, M. E., Bradley, C. A. 2010. Potential viral threats to *Miscanthus×giganteus* and switchgrass production for bioenergy in the United States. Phytopathology 100:S3.

Ahonsi, M. O., Agindotan, B. O., Arundale, R., Gray, M. E., Voigt, T. B., and Bradley, C. A. 2010. First report of *Pithomyces chartarum* causing a leaf blight of *Miscanthus× giganteus* in Kentucky. Plant Dis. 94:480.

Andersen, B., Kroger, E., and Roberts, R. G. 2001. Chemical and morphological segregation of *Alternaria alternate, A. gaisen* and *A. longipes*. Mycol. Res. 105:291-299.

Anderson, W. F., and Akin, D. E. 2007. Structural and chemical properties of grass lignocelluloses related to conversion for biofuels. J. Ind. Microbiol. Biotechnol. 35:355-366.

Anonymous. 1960. Index of Plant Diseases in the United States. U.S.D.A. Agric. Handb. 165:1-531.

Bennett, F. T. 1937. *Sclerotinia homoeocarpa*. Annals Appl. Biol. 24:236.

Boerner, R. E. 1992. Plant life span and response to inoculation with vesicular-arbuscular mycorrhizal fungi. I. Annual versus perennial grasses. Mycorrhiza 1:153-161.

Booth, C. 1971. The genus *Fusarium*. Commonwealth Mycological Institute: 157-179.

Booth, C. 1971. The genus *Fusarium*. Commonwealth Mycological Institute. Kew, Surrey, England.

Bouton, J. 2008. Improvement of switchgrass as a bioenergy crop. Gen. Improv. Bioenerg. Crops 11:296-308.

Brejda, J. J., Moser, L. E., and Vogel, K. P. 1998. Evaluation of switchgrass rhizosphere microflora for enhancing seedling yield and nutrient uptake. Agron. J. 90:753-758.

Brunken, J. N., and Estes, J. R. 1975. Cytological and morphological variation in *Panicum virgatum* L. Southwestern Naturalist 19:379-385.

Carris, L. M., Castlebury, L. A., and Zale, J. 2008. First report of *Tilletia pulcherrima* bunt on switchgrass (*Panicum virgatum*) in Texas. Plant Dis. 92:1707.

Carris, L. M., Castlebury, L. A., and Zale, J. 2008. First report of *Tilletia pulcherrima* on switchgrass (*Panicum virgatum* L.) in Texas. Plant Dis. 92:1707.

Cassida, K. A. Kirkpatrick, T. L., Robbins, R. T., Muir, J. P., Venuto, B. C., and Hussey, M. A. 2005. Plant-parasitic nematodes associated with switchgrass (*Panicum virgatum* L.) grown for biofuel in the south central United States. Nematropica 35:1-10.

Chawla, A. S., Singh, M., Murthy, M. S., Gupta, M. P., and Singh, H. 1987. Anti-inflammatory action of ferulic acid and its esters in carrageenan-induced rat paw edema model. Indian J. Exp. Biol. 25:187-189.

Chen, S. F., Mowery, R. A., Scarlata, C. J., and Chambliss, C. K. 2007. Compositional analysis of water-soluble materials in corn stover. J. Agric. Food Chem. 55:5912-5918.

Chen, S. F., Mowery, R. A., Sevcik, R. S., Scarlata, C. J., and Chambliss, C. K. 2010. Compositional analysis of water-soluble materials in switchgrass. J. Agric. Food Chem. 58:3251-3258.

Choudhry, A., Tucci, V., and Greene, J. N. 2010. Disseminated Bipolaris infection. Infect. Dis. Clin. Pract. 19:204-207.

Clark, R. B., and Zeto, S. K. 2000. Mineral acquisition by arbuscular mycorrhizal plants. J. Plant Nutrition 23:867-902.

Clay, K. 1988. Fungal endophytes of grasses: a defensive mutualism between plants and fungi. Ecology 69:10-16.

De Luna, L. Z., Watson, A. K., and Paulitz, T. C. 2002. Reaction of rice (*Oryza sativa*) cultivars to penetration and infection by *Curvularia tuberculate* and *C. oryzae*. Plant Dis. 86:470-476.

Dee, M. M. and T. Russell assisted in collection and identification of *Alternaria alternate*. J. Zale, K. D. Gwinn, and B. H. Ownley provided guidance and funding for the studies.

Dee, M. M., R. J. Gualandi, Jr., and S. Huff assisted in fungal collection, isolation and morphological identification of *Bipolaris spicifera*, and determination of pathogenicity.

Doohan, F. M., Brennan, J., and Cooke, B. M. 2003. Influence of climatic factors on *Fusarium* species pathogenic to cereals. Eur. J. Pl. Pathol. 109:755-768.

Eken, C., Jochum, C. C., Yuen, G. Y. 2006. First report of leaf spot of smooth bromegrass caused by *Pithomyces chartarum* in Nebraska. Plant Dis. 90:108.

Ellis., M. B. 1971. Dematiaceous Hyphomycetes. Commonwealth Mycological Institute, Kew, Surrey, UK.

Etheridge, J. V., Davey, L., and Christian, D. G. 2001. First report of *Rhizoctonia cerealis* causing sharp eyespot in *Panicum virgatum* in the UK. New Dis. Rep. 3:17.

Farr, D. F., and Rossman, A. Y. 2011. Fungal Databases, Systematic Mycology and Microbiology Laboratory, ARS, USDA. Retrieved Aug. 4, 2011, from http://nt.ars-grin.gov/fungaldatabases/.

Farr, D. F., and Rossman, A. Y. Fungal Databases, Systematic Mycology and Microbiology Laboratory ARS, USDA. Retrieved Oct. 28, 2011. <http://nt.ars-grin.gov/fungaldatabases/>.

Fernandez, M. R. and Heath, M. C. 1989. Interaction of the non-host French bean plant (*Phaseolus vulgaris*) with parasitic and saprophytic fungi. III. Cytologically detectable responses. Can. J. Bot. 67:676-686.

Garrett, K. A., Dendy, S. P., Power, A. G., Blaisdell, G. K., Alexander, H. M., and McCarron, J. K. 2004. Barley yellow dwarf disease in natural populations of dominant tallgrass prairie species in Kansas. Plant Dis. 88:574.

Ghimire, S. R., Charlton, N. D., Bell, J. D., Krishnamurthy, Y. L., and Craven, K. D. 2011. Biodiversity of fungal endophyte communities inhabiting switchgrass (*Panicum virgatum* L.) growing in native tallgrass prairie of northern Oklahoma. Fung. Diversity 47:19-27.

Gibson, D. M., King, B. C., Hayes, M. L., and Bergstrom, G. C. 2011. Plant pathogens as a source of diverse enzymes for lignocellulose digestion. Curr. Opinion Microbiol. 14:264-270.

Graf, E. 1992. Antioxidant potential of ferulic acid. Free Radical Biolog. Med. 13:435-448.

Gravert, C. E. and Munkvold, G. P. 2002. Fungi and diseases associated with cultivated switchgrass in Iowa. J. Iowa Acad. Sci. 109:30-34.

Gwinn, K. D., Trigiano, R. N., Gavin, A. M., and Conger, B. V. 1991. Bacterial interference with in vitro assays of tall fescue seeds for *Acremonium coenophialum*. Crop Sci. 31:1369-1370.

Heath, M. C. 1980. Reactions of nonsuscepts to fungal pathogens. Annu Rev. Phytopathol. 18:211-36.

Herald, P. J., and Davidson, P. M. 1983. Antibacterial activity of selected hydroxycinnamic acids. J. Food Sci. 48:1378-1379.

Hetrick, B. A., Kitt, D. G., and Wilson, G. T. 1988. Mycorrhizal dependence and growth habit of warm-season and cool-season tallgrass prairie plants. Can. J. Botany. 66:1376-1380.

Hu, H., Hang, B., and Wang, P. 1990. Anti-inflammatory effects of ferulic acid. Zhongguo Yaoke Daxue Xuebao 21:279-282.

Jung H G, AC Shalita-Jones. 1990. J. Agric. Food Chem. 38, 397-402.

Kavroulakis, N., Ntougias, S., Zervakis, G. I., Ehaliotis, C., Haralampidis, K., and Papadopoulou, K. K. 2007. Role of ethylene in the protection of tomato plants against soilborne fungal pathogens conferred by an endophytic *Fusarium solani* strain. J. Exp. Bot. 58:3853-3864.

Keshwani, D. R., and Cheng, J. J. 2009. Switchgrass for bioethanol and other value-added applications: A review. Bioresource Technol. 100:1515-1523.

Kikuzaki, H., Hisamoto, M., Hirose, K., Akiyama, K., and Taniguchi, H. 2002. Antioxidant properties of ferulic acid and its related compounds. J. Agric. Food Chem. 50:2161-2168.

Kim S, N Moustaid-Moussa. 2000. J. Nutr. 130, 3110S-3115S.

Kirk, P. 2011. Index Fungorum. CABI, retrieved Oct. 31, 2011.

Koo, H. M., Lee, S. H., Chung, I. M., and Chun, S. E. 2004. Cultural characteristics of a seedborne fungus, *Bipolaris spicifera* detected from imported grass seeds into Korea. Mycobiology 32:186-189.

Krupinsky, J. M., Berdahl, J. D., Schoch, C. L., and Rossman, A. Y. 2004. Leaf spot on switchgrass (*Panicum virgatum*), symptoms of a new disease caused by *Bipolaris oryzae*. Can. J. Plant Pathol. 26:371-378.

Kusaba, M., and Tsuge, T. 1995. Phylogeny of *Alternaria* fungi known to produce host-specific toxins on the basis of variation in internal transcribed spacers of ribosomal DNA. Curr. Genet. 28:491-498.

Leslie, J. F., and Summerell, B. A. 2006. The *Fusarium* Laboratory Manual. Blackwell Publishing. Ames, Iowa.

Lockwood, J. L. 1988. Evolution of concepts associated with soilborne plant pathogens. Annu Rev. Phytopathol. 26:93-121.

Li, K. N., Rouse, D. I., and German, T. L. 1994. PCR primers that allow intergeneric differentiation of ascomycetes and their application to *Verticillium* spp. Appl. Environ. Microbiol. 60:4324-4331.

Liu, G. T., Qian, Y. Z., Zhang, P., Dong, W. H., Qi, Y. M., and Guo, H. T. 1992. Etiological role of *Alternaria alternata* in human esophageal cancer. Chin. Med. J. 105:394-400.

Liu, G. T., Qian, Y. Z., Zhang, P., Dong, Z. M., Shi, Z. Y., Zhen, Y. Z., Miao, J., and Xu, Y. M. 1991. Relationships between *Alternaria alternata* and oesophageal cancer. IARC Sci Publ. 105:258-262.

Liu, Y. 1987. Pharmaceutical composition for increasing immunity and decreasing side effects of anticancer chemotherapy. U.S. Pat. No. 4,687,761. Marrone Biolnnovations. 2009. Retrieved Oct. 31, 2011. <http://www.marrone-bioinnovations.com/products/regalia/>.

Mandal, S., Mitra, A., and Mallick, N. 2009. Time course study on accumulation of cell wall-bound phenolics and activities of defense enzymes in tomato roots in relation to *Fusarium* wilt. World J. Microbiol. Biotechnol. 25:795-802.

Mathur, S. B., and Kongsdal, O. 2003. Common Laboratory Seed Health Testing Methods for Detecting Fungi. International Seed Testing Association, Basserdorf, CH-Switzerland.

Meehan, F. 1947. A host index to seed-borne species of *Helminthosporium* and *Curvularia* on certain grasses. Proc. Assoc. Offic. Seed Analysts 37:89-92.

Mekete, T., Reynolds, K., Lopez-Nicora, H. D., Gray, M. E., and Niblack, T. L. 2011. Plant-parasitic nematodes are potential pathogens of *Miscanthus×giganteus* and *Panicum virgatum* used for biofuels. Plant Dis. 95:413-418.

Misaghi, I. J., Grogan, R. G., Duniway, J. M., and Kimble, K. A. 1978. Influence of environment and culture media on spore morphology of *Alternaria alternate*. Phytopathology 68:29-34.

Nelson, P. E., Toussoun, T. A., and Marassas. 1983. *Fusarium* species, an illustrated manual for identification. Pennsylvania State University, University Park and London: 89-100.

Nicholson, R. L., and Hammerschmidt, R. 1992. Phenolic compounds and their role in disease resistance. Annu Rev. Phytopathol. 30:369-389.

Nyvall, R. F. and Percich, J. A. 1999. Development of fungal brown spot and spot blotch on cultivated wild rice in Minnesota. Plant Dis. 83:936-938.

Panina, Y, D R Fravel, C J Baker, L A Shcherbakova. 2007. J. Phytopathology 155, 475-481.

Parrish, D. J., and Fike, J. H. 2005. The biology and agronomy of switchgrass for biofuels. Crit. Rev. Plant Sci. 24:423-459.

Parry, D. W., Pettitt, T. R., Jenkinson, P., and Lees, A. K. 1995. The cereal *Fusarium* complex. Pages 301-320 in: Ecology of Plant Pathogens, P. Blakeman and B. Willamson, eds. CAB International, Wallingford, UK.

Peet, R. K. 1974. The measurement of species diversity. Ann. Rev. Ecol. System. 5:285-307.

Porter, C. L. 1966. An analysis of variation between upland and lowland switchgrass *Panicum virgatum* L. in central Oklahoma. Ecology 47:980-992.

Pryor, B. M., and Gilbertson, R. L. 2000. Molecular phylogenetic relationships amongst *Alternaria* species and related fungi based upon analysis of nuclear ITS and mt SSU rDNA sequences. Mycol. Res. 104:1312-1321.

Pryor, B. M., and Gilbertson, R. L. 2002. Relationships and taxonomic status of *Alternaria radicina, A. carotiincultae*, and *A. petroselini* based upon morphological, biochemical, and molecular characteristics. *Mycologia* 94:49-61.

Randoux, B., Renard, D., Nowak, E., Sanssene, J., Courtois, J., Durand, R. and Reignault, P. 2006. Inhibition of *Blumeria graminis* f. sp. *tritici* germination and partial enhancement of wheat defenses by Milsana. Phytopathology 96:1278-1286.

Ravindranath, S. V., Uppugundla, N., Lay, J. O., Clausen, E. C., Wilkins, M. Inghraham, R. G., West, C., Wu, Y., and Carrier, D. J. 2009. Policosanol, α-tocopherol, and moisture content as a function of timing of harvest of switchgrass (*Panicum virgatum* L.). J. Agric. Food Chem. 57:3500-3505.

Ray, R. C., and Raavi, V. 2005. Post-harvest spoilage of sweet potato in tropics and control measures. Crit. Rev. Food Sci. Nutr. 45:623-644.

Roberts, R. G., Reymond, S. T., and Andersen, B. 2000. RAPD fragment pattern analysis and morphological segregation of small-spored *Alternaria* species and species groups. Mycol. Res. 104:151-160.

Sanderson, M. A., Adler, P. R., Boateng, A. A., Casler, M. D. and Sarath, G. 2006. Switchgrass as a biofuels feedstock in the USA. Can. J. Plant Sci. 86:1315-1325.

Schmer, M. R., Vogel, K. P., Mitchell, R. B., and Perrin, R. K. 2008. Net energy of cellulosic ethanol from switchgrass. PNAS 105:464-469.

Shahin, E. A., and Shephard, J. F. 1979. An efficient technique for inducing profuse sporulation of *Alternaria* species. Phytopathology 69:618-620.

Sill, W. H. 1957. *Panicum* mosaic, a new virus disease of *Panicum virgatum* and related grasses. Phytopathology 47:31.

Sivanesan, A. 1987. Graminicolous species of *Bipolaris, Curvularia, Drechslera, Exserohilum* and their teleomorphs, Mycolog. Pap. 158:201.

Sivanesan, A. and P. Holliday. 1981. *Cochliobolus sativus*. CMI Descr. Pathog. Fungi bact. 71:701.

Sutton, J. C. 1982. Epidemiology of wheat head blight and maize ear rot caused by *Fusarium graminearum*. Can. J. Plant Pathol. 4:195-209.

Tao, L., Aden, A., Elander, R. T., Pallapolu, V. R., Lee, Y. Y., Garlock, R. J., Balan, V., Dale, B. E., Kim, Y. K., Mosier, N. S., Ladish, M. R., Falls, M., Holtzapple, M. T., Sierra, R., Shi, J., Ebrik, M. A., Redmond, T., Yang, B., Wyman, C. E., Hames, B., Thomas, S, and Waner, R. E. 2011. Process and technoeconomic analysis of leading pretreatment technologies for lignocellulosic ethanol production using switchgrass. Bioresource Technol. doi: 10.1016/j.biortech.2011.07.051.

Thammasouk, K., Tandjo, D., and Penner, M. H. 1997. Influence of extractives on the analysis of herbaceous biomass. J. Agric. Food Chem. 45:437-443.

Thomma, B. P. 2003. *Alternaria* spp.: from general saprophyte to specific parasite. Molec. Plant Pathol. 4:225-236.

Tomaso-Peterson, M., and Balbalian, C. J. 2010. First report of *Bipolaris oryzae* causing leaf spot of switchgrass in Mississippi. Plant Dis. 94:643.

Uppugundla, N., Engelberth, A., Ravindranath, S. V., Clausen, E. C., Lay, J. O., Gidden, J., and Carrier, D. J. 2009. Switchgrass water extracts: Extraction, separation and biological activity of rutin and quercitrin. J. Agric. Food Chem. 57:7763-7770.

Yan, J., Hu, Z., Pu, Y., Brummer, E. C., and Ragauskas, A. J. 2010. Chemical compositions of four switchgrass populations. Biomass and Bioenergy. 34:48-53.

Vogel, K. P. 2004. Switchgrass. Pages 561-588 in: Warm-season (C4) grasses. Agron. Monogr. 45. ASA, CSSA, and SSSA, L. E. Moser, B. L. Burson and L. E. Sollenberger, eds. Madison, Wis.

Vu, A. L., Dee, M. D., Russell, T., Zale, J., Gwinn, K. D., and Ownley, B. H. First report of leaf spot caused by *Alternaria alternate* on switchgrass in Tennessee. Plant Dis. (Accepted).

Vu, A. L., Dee, M. M., Gualandi, Jr., R. J., Huff, S., Zale, J., Gwinn, K. D., and Ownley, B. H. 2011. First report of leaf spot caused by *Bipolaris spicifera* on switchgrass in the United States. Plant Dis. 95:1191.

Vu, A. L., Gwinn, K. D., and Ownley, B. H. 2011. First report of *Sclerotinia homoeocarpa* causing dollar spot on switchgrass in the United States. Plant Dis. 95:1585.

Vu, A. L., Gwinn, K. D., and Ownley, B. H. 2011. First report of spot blotch and common root rot caused by *Bipolaris sorokiniana* on switchgrass in Tennessee. Plant Dis. 95:1195.

Walker, J. R. 1994. Antimicrobial compounds in food plants. Pages 181-204 in: Natural Antimicrobial Systems and Food Preservation. V. M. Dillon and R. G. Board, eds., CAB International, Wallingford, UK.

Waterhouse, A. L. 2002. Determination of total phenolics. Current Protocols in Food Analytical Chemistry 1.1.1-1.1.8.

Waxman, K. D., and Bergstrom, G. C. 2011. First report of a leaf spot caused by *Bipolaris oryzae* on switchgrass. Plant Dis. 95:1192.

Welbaum, G. E., Sturz, A. V., Dong, Z., and Nowak, J. 2004. Managing soil microorganisms to improve productivity of agro-ecosystems. Crit. Rev. Plant Sci. 23:175-193.

Weller, D. M., Raaijmakers, J. M., McSpadden-Gardener, B. B., Thomashow, L. S. 2002. Microbial populations responsible for specific soil suppressiveness to plant pathogens. Annu Rev. Phytopathol. 40:309-48.

White, T. J. 1990. Page 315 in: PCR Protocols: A Guide to Methods and Applications. M. A. Innis et al., eds., Acad. Press, NY.

Wolfe, M. S. 2000. Crop strength through diversity. Nature 406:681-682.

Zale, J., Freshour, L., Agarwal, S., Sorochan, J., Ownley, B. H., Gwinn, K. D., Castlebury, L. A., and Carris, L. M. 2008. First report of *Puccinia emaculata* on switchgrass (*Panicum virgatum* L.) in Tennessee. Plant Dis. 92:1710.

We claim:

1. A method of preventing or treating an infection by an infectious agent in a plant, the method comprising administering an effective amount of a solvent soluble switchgrass extract to the plant, wherein the solvent is ethanol and the infectious agent is a bacterium.

2. The method of claim 1, wherein the plant is a tomato plant.

3. The method of claim 1, wherein the bacterium is selected from *Clavibacter michiganensis* subsp. *michiganensis, Xanthomonas perforans, Pseudomonas syringae* pv. tomato and *Pseudomonas mediterranea*.

* * * * *